(12) United States Patent
Greffe et al.

(10) Patent No.: US 7,087,746 B2
(45) Date of Patent: Aug. 8, 2006

(54) FUNCTIONALISED MALTOSYL FLUORIDE AS GLYCOSYL DONOR IN THE CHEMO-ENZYMATIC PREPARATION OF RATIO OF OLIGO-OR POLYSACCHARIDES

(75) Inventors: Lionel Greffe, Chatte (FR); Hugues Driguez, Grenoble (FR)

(73) Assignee: Centre National de la Recherche Scientifique (C.N.R.S.), Paris (FR)

( * ) Notice: Subject to any disclaimer, the term of this patent is extended or adjusted under 35 U.S.C. 154(b) by 37 days.

(21) Appl. No.: 10/482,957

(22) PCT Filed: Jul. 26, 2002

(86) PCT No.: PCT/FR02/02695

§ 371 (c)(1), (2), (4) Date: Jan. 8, 2004

(87) PCT Pub. No.: WO03/010178

PCT Pub. Date: Feb. 6, 2003

(65) Prior Publication Data

US 2004/0176317 A1    Sep. 9, 2004

(30) Foreign Application Priority Data

Jul. 26, 2001  (FR) .................................. 01 10018

(51) Int. Cl.
*C13K 7/00* (2006.01)
*C12P 19/18* (2006.01)

(52) U.S. Cl. .................... 536/123.13; 435/96; 435/97; 435/101

(58) Field of Classification Search ........... 536/123.13; 435/100, 96, 97, 101
See application file for complete search history.

(56) References Cited

U.S. PATENT DOCUMENTS 6,066,782 A * 5/2000 Kossmann et al. ......... 800/284

FOREIGN PATENT DOCUMENTS

JP  1098498 A2 * 4/1989

OTHER PUBLICATIONS

Apparu et al., A Highly Efficient Chemoenzymatic Synthesis of 6A,6D-dideoxy-6A, 6D-diiodo alpha cylodextrin., 1995., Carbhydrate Letter vol. 1, pp. 349-352.*

Cottaz et al. Chemoenzymatic Approach to the Preparation of Regioselctively Modified Cyclodextrins. The Substrate Specificity of the Enzyme Cyclodextrin Glucosyltransferase (CGTase). 1991., J. Chem Soc. Perkin Trans 1. pp. 2235-2241.*

Faijes et al. Oligosaccharide Synthesis by Coupled endo-Glycosynthases of Different Specificit: A Straightforward Preparation of Two Mixed-Linkage Hexasaccharide Substrates of 1,3/1,4-B-Glucanases. 2001. Chem. Eur J. 7, No. 21. pp. 4651-4655.*

Fort et al. Highly Efficient Synthesis of B(1-4)-Oligo- and -Polysacharides Using Mutant Cellulase. 2000. J. Am. Chem. Soc. 122. pp. 5429-5437.*

C. Apparu et al.:, "A highly effieicent chemoenzymatic synthesis of 6A, 6D-diiode alfa-cyclodextrin" Carbohydrate Letters, vol. 1, 1995, pp. 349-352, XP008003716, le document en entier.

S. Fort et al.:, "Stepwise synthesis of cellodextrins assisted by a mutant cellulase", Israel Journal of Chemistry, vol. 40, 2000, pp. 217-221, XP008003718 le document en entier.

S.-I. Shoda et al.., "Enzymatic polymerization of activated glycosyl monomers for highly selective polysaccharide synthesis", Korea Polmer Journal, vol. 4, No. 2, 1996, pp. 112-116, XP008003717 le document en entier.

Bornaghi L et al:, "Transfer reactions catalyzed by cyclodextrin glucosyltransferase using 4-thiomaltosyl and C-maltosyl fluorides as artificial donors", Carbohydrate Research, Elsevier Scientific Publishing Company. Amsterdam, NL, vol. 305, No. 3-4, Dec. 1997, pp. 56 1-568, XP004191939, ISSN: 0008-6215, le document en entier.

* cited by examiner

*Primary Examiner*—Leigh C. Maier
(74) *Attorney, Agent, or Firm*—Young & Thompson

(57) ABSTRACT

Disaccharides of formula (I) are derived from a-maltosyl fluoride, wherein $R^1$ and $R^2$ are defined. Such disaccharides are useful as glycosyl donors in transglycosylation reactions catalyzed by glycoside-hydrolazes or in transfer reactions catalyzed by transglycosylases during the preparation of oligosaccharides or polysaccharides.

25 Claims, No Drawings

FUNCTIONALISED MALTOSYL FLUORIDE AS GLYCOSYL DONOR IN THE CHEMO-ENZYMATIC PREPARATION OF RATIO OF OLIGO-OR POLYSACCHARIDES

The invention relates to a family of disaccharides derived from α-maltosyl fluoride which can be used as glycosyl donors in the chemoenzymatic synthesis of oligo- and polysaccharides catalyzed by enzymes of glycoside-hydrolase and transglycosylase type.

The process of the invention makes possible in particular the sequential and linear elongation of an oligosaccharide and/or polysaccharide recognized as glycosyl acceptor by enzymes of glycoside hydrolase or transglycosylase type.

Glycosyl fluorides have been known for a long time to be good glycosyl donors and are commonly used in transglycosylation reactions catalyzed by glycoside hydrolases or transglycosylases.

The studies by Hehre, published in Arch. Biochem. Biophys., 135 (1969), 75; Arch. Biochem. Biophys., 142 (1971), 382; and Carbohydr. Res., 26 (1973), 240, have shown in particular that amylases are capable of using glycosyl fluorides to form condensation products. In 1978, the Hehre team published, in Carbohydr. Res., 61, 1978, 291–299, a study using α-maltosyl fluoride as substrate for β-amylases. Subsequently, Hehre used various strains of α-amylase, including the α-amylase resulting from *Aspergillus oryzae*, for the synthesis of maltooligosaccharides from α-maltosyl and observed that these enzymes exhibit a preferential non-hydrolytic activity since very little hydrolysis product, maltose, is finally isolated (cf. Carbohydr. Res., 71, 1979, 287–298).

In the same way, Okada et al. demonstrate that the production of 6-O-maltosyl-cyclodextrins is possible using the transfer of α-maltosyl fluoride to a cyclodextrin using a pullulanase (protein belonging to the family of the α-amylases).

One of the main disadvantages of this method is the isolation of complex mixtures of 6-O-maltosyl-cyclodextrins resulting from the multisubstitution of the cyclodextrins and from the uncontrolled elongation of the polymer chains.

The use of modified α-maltosyl fluoride has also been described in the art. Driguez et al. have published in particular the synthesis of $6^A,6^C,6^E$-tri-O-methyl-cyclomaltohexaose by condensation and cyclization of 6'-O-methyl-α-maltosyl fluoride by cyclodextrin glucosyltransferase (cGTase). The authors demonstrate the possibility of preparing mixtures of substituted cyclodextrins (α, β, γ) in the presence of cGTase and of one of the following maltosyl fluorides (1) or (2) optionally modified in the 6 position: J. Chem. Soc., 16, 1989, 1088–1089.

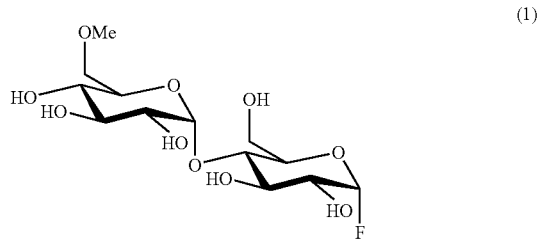

(1)

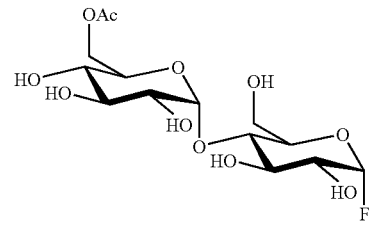

(2)

These modified maltosyl fluorides are recognized both as glycosyl donors and acceptors by cGTase.

Bornaghi et al. describe the synthesis of hemithiomaltodextrins and hemi-C-maltooligosaccharides from 4-thio-α-maltosyl fluoride (3) and α-C-maltosyl fluoride (4) and in the presence of cGTase: Carbohydr. Res., 305, 1997, 561–568.

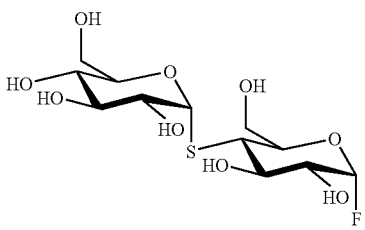

(3)

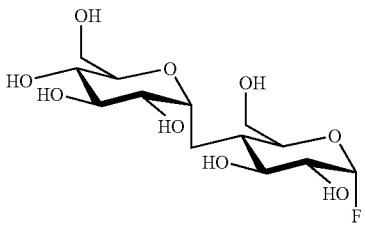

(4)

However, the reaction products are in fact mixtures in each case.

The fluoride 3 in the presence of cGTase allows the authors, after acetylation, to obtain acetylated 4-thiomaltose (42%) (hydrolysis product), acetylated hemithiomaltohexaose (4%), acetylated cyclo-α-(1–4)-thiomaltotetraoside (13%), acetylated cyclo-α-(1–4)-thiomaltopentaoside (16%) and acetylated cyclo-α-(1–4)-4-thiomaltohexaoside (7%). By using 3 equivalents of 4-thiomaltose as glycosyl acceptor, the authors isolated hemithiomaltotetraose (18%) and hemithiomaltohexaose (14%).

The fluoride 4 in buffered solution and in the presence of cGTase does not allow the authors to obtain transglycosylation products but only the hydrolysis product. By using an aqueous/organic medium, the authors succeeded in limiting the hydrolysis reaction of the substrate. They thus obtained, after acetylation, acetylated hemi-C-maltotetraose (18%), acetylated hemi-C-maltohexaose (11%) and acetylated hemi-C-maltooctaose (5%). It should be noted here that the amount of hydrolyzed substrate is high (respectively 42 and 66%).

In addition, the synthesis of 4'-deoxymaltosyl fluoride and 4"-deoxymaltotriosyl fluoride by Withers et al. (Carbohydr. Res., 268, 1995, 93–106) may be pointed out, these two compounds, however, never having been used for synthetic purposes with a view to the preparation of oligo- or polysaccharides.

The modified maltosyl fluorides of the invention operate as glycosyl donors for enzymes of glycoside hydrolase type or of transglycosylase type. The modifications made to the $4^{II}$ position or $4^{II}$ and $6^{II}$ positions of the maltosyl fluoride make possible the simple conversion of these glycosyl donors to glycosyl acceptors, so that a step-by-step synthesis of oligosaccharides and of polysaccharides is rendered possible without the risk of uncoordinated growth of the polysaccharide chains.

The process of the invention thus makes possible ideal control of the synthesis of oligo- or polysaccharides.

More specifically, the invention relates to a disaccharide of formula I:

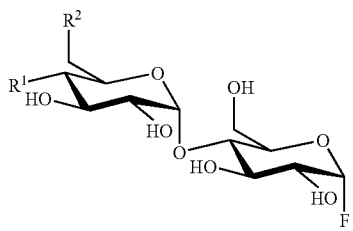

I derived from α-maltosyl fluoride, in which:

$R^1$ and $R^2$, which are identical or different, represent a functional organic group, optionally protected, attached to the glycoside unit via a nitrogen atom, an oxygen atom, a sulfur atom or a halogen atom, or else $R^1$ and $R^2$ together form a functional organic group, optionally protected, attached to the glycoside unit via two atoms selected from oxygen, sulfur and nitrogen atoms, it being understood that $R^1$ does not represent a hydroxyl group.

The configuration of the endocyclic asymmetric carbons of the compounds of formula I is that of the corresponding carbons of the α-maltosyl.

The functional organic group representing $R^1$ and/or $R^2$ is of any nature, provided that this group does not interfere with the subsequent condensation reaction involving the corresponding disaccharide of formula I as starting reactant and provided that $R^1$ can be converted to a group which allows the resulting disaccharide to be a glycosyl acceptor. A glycosyl acceptor is understood here as meaning a molecule which positions itself in the acceptor subsites of the enzyme.

Examples of groups which allow the resulting disaccharide to be a glycosyl acceptor are the OH, $NH_2$ and SH radicals. Thus, $R^1$ is generally the precursor of an OH, SH or $NH_2$ group.

According to the invention, $R^1$ does not represent a hydroxyl group. Nevertheless, $R^1$ can represent a hydroxyl group protected by any protective group used in organic chemistry, such as one of those described in Protective Groups in Organic Synthesis, Green T. W. and Wutz P. G. M, published by John Wiley & Sons, 1991, or in Protecting Groups, Kocienski P. J., 1994, Georg Thieme Verlag.

Conversely, $R^2$ can represent a free hydroxyl group or else a hydroxyl group protected by a protective group, such as those described in the two works mentioned above.

A preferred group of disaccharides of formula I is composed of the disaccharides in which $R^2$ represents —OH.

Protective groups for the hydroxyl functional group are in particular the ether, ester, sulfonate, carbamate, acetal, hemiacetal and carbonate groups.

Mention may be made, as examples of meanings of $R^1$ and/or $R^2$, of the following groups: optionally substituted alkoxy; optionally substituted alkenyloxy; optionally substituted aryloxy; optionally substituted diarylalkoxy; or optionally substituted triarylalkoxy; optionally substituted heteroaryloxy; optionally substituted arylalkoxy; optionally substituted heteroarylalkoxy; optionally substituted alkylcarbonyloxy; optionally substituted arylcarbonyloxy; optionally substituted heteroarylcarbonyloxy; optionally substituted arylalkylcarbonyloxy; optionally substituted heteroarylalkylcarbonyloxy; optionally substituted alkylsulfonyloxy; optionally substituted arylsulfonyloxy; optionally substituted heteroarylsulfonyloxy; optionally substituted arylalkylsulfonyloxy; optionally substituted heteroarylalkylsulfonyloxy; —O—$SiR^fR^gR^h$, where $R^f$, $R^g$ and $R^h$ are selected independently from optionally substituted alkyl and aryl; —O—CO—$NR^aR^b$, where $R^a$ and $R^b$ are selected independently from optionally substituted alkyl, optionally substituted aryl, optionally substituted arylalkyl, optionally substituted heteroarylalkyl and a hydrogen atom; and

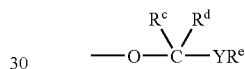

where $R^c$ and $R^d$ are as defined above for $R^a$ and $R^b$ or else $R^c$ and $R^d$ together form an optionally substituted alkylene chain and $R^e$ is as defined above for $R^a$, or else $R^d$ and $R^e$ together form an optionally substituted alkylene chain, $R^c$ being as defined above for $R^a$; and Y represents O or S.

According to the invention, $R^1$ and/or $R^2$ can represent a halogen atom, such as, for $R^1$, a bromine, chlorine or iodine atom, and, for $R^2$, a chlorine, bromine, iodine or fluorine atom.

In an alternative form, $R^1$ and/or $R^2$ can represent an amine or thiol functional group optionally substituted or protected by one or two of the protective groups described in Protective Groups in Organic Synthesis, Greene T. W. and Wutz P. G. M., published by John Wiley & Sons, 1991, or in Protecting Groups, Kocienski P. J., 1994, Georg Thieme Verlag.

Such protective groups are in particular carbamate, amide, azide, urea, thioacetate, disulfide, thiourea, arylthio, alkylthio, acylthio, arylcarbonylthio, acetamido or benzamido groups.

Mention may be made, as examples of meanings of $R^1$ and $R^2$, of the following groups: amino; alkylamino; dialkylamino; —NH—CO—$R^a$, where $R^a$ is as defined above; azide; —$NR^a$—CO—$NR^bR^f$, where $R^a$ and $R^b$ are as defined above and $R^f$ takes any one of the meanings given above for $R^a$; —O—CO—NH—$R^a$, $R^a$ being as defined above; —S—$R^a$, $R^a$ being as defined above; and —$NR^a$—CO—$R^e$, $R^a$ and $R^e$ being as defined above.

In an alternative form, the $R^1$ and $R^2$ groups can together form an optionally protected functional organic group.

Such a functional group is, for example, a protective group for a diol functional group, such as an alkylidenedioxy group which is optionally substituted and, for example, substituted by aryl.

Thus, $R^1$ and $R^2$ can together form an O-isopropylidene or O-benzylidene group.

A particularly preferred disaccharide is the disaccharide of formula I in which $R^1$ represents a 2-tetrahydropyranyl group and, preferably, $R^2$ represents a hydroxyl group.

A disaccharide which is also preferred is the disaccharide of formula I in which $R^1$ represents a 2-tetrahydropyranyl group and $R^2$ represents a halogen atom, such as bromine.

Mention may be made, as other preferred saccharide, of the disaccharide of formula I in which $R^1$ represents optionally substituted amino or azido and $R^2$ represents optionally substituted amino or azido.

Another preferred disaccharide is that of formula I in which $R^1$ represents optionally substituted amino or azido and $R^2$ represents —OH.

More particularly, preference is given to the disaccharides for which, in the formula I:

$R^1$=NH$_2$ or azido; $R^2$=OH; or
$R^1$=NH$_2$ or azido; $R^2$=NH$_2$ or azido.

Preferred substituents of the amino group are alkyl, aryl and arylalkyl groups in which aryl is optionally substituted.

In the context of the invention, the term "alkyl" is understood to mean a linear or branched hydrocarbonaceous chain comprising from 1 to 14 carbon atoms, preferably from 1 to 10, better still from 1 to 6 carbon atoms, for example from 1 to 4 carbon atoms.

Examples of alkyl radicals are methyl, ethyl, propyl, isopropyl, butyl, isobutyl, t-butyl, pentyl, isopentyl, neopentyl, 2-methylbutyl, 1-ethylpropyl, hexyl, isohexyl, neohexyl, 1-methylpentyl, 3-methylpentyl, 1,1-dimethylbutyl, 1,3-dimethylbutyl, 2-ethylbutyl, 1-methyl-1-ethylpropyl, heptyl, 1-methylhexyl, 1-propylbutyl, 4,4-dimethylpentyl, octyl, 1-methylheptyl, 2-methylhexyl, 5,5-dimethylhexyl, nonyl, decyl, 1-methylnonyl, 3,7-dimethyloctyl and 7,7-dimethyloctyl.

The term "aryl" is understood to mean, according to the invention, a preferably $C_6$–$C_{18}$, aromatic, mono- or polycyclic (for example, mono- or bicyclic) hydrocarbonaceous group, such as phenyl, naphthyl, anthryl or phenanthryl.

The heteroaryl groups are monocyclic or polycyclic aromatic heterocyclic groups comprising heteroatoms generally selected from O, S and N, optionally in the oxidized state (case of S and of N).

Preferably, the heteroaryl is mono-, bi- or tricyclic.

Preferably, at least one of the monocycles constituting the heterocycle comprises from 1 to 4 endocyclic heteroatoms, better still from 1 to 3 heteroatoms.

Preferably, the heterocycle is composed of one or more monocycles each having from 5 to 7 ring members.

Examples of monocyclic heteroaryls comprising 5 to 7 ring members are in particular pyridine, furan, thiophene, pyrrole, pyrazole, imidazole, thiazole, isoxazole, furazan, pyridazine, pyrimidine, pyrazine, thiazines, oxazole, pyrazole, oxadiazole, triazole and thiadiazole.

Examples of bicyclic heteroaryls in which each monocycle comprises from 5 to 7 ring members are selected from indolizine, indole, isoindole, benzofuran, benzothiophene, indazole, benzimidazole, benzothiazole, benzofurazan, benzothiofurazan, purine, quinoline, isoquinoline, cinnoline, phthalazine, quinazoline, quinoxaline, naphthyridines, pyrazolo-triazine (such as pyrazolo[1,3,4]triazine), pyrazolo-pryrimidine and pteridine.

The tricyclic heteroaryls in which each monocycle comprises from 5 to 7 ring members are, for example, selected from acridine, phenazine or carbazole.

Alkylene defines an optionally substituted, linear or branched, preferably $C_1$–$C_{14}$, divalent hydrocarbonaceous group derived from an alkyl group by removal of a hydrogen atom. Alkylene advantageously denotes a $C_1$–$C_{10}$ group, better still a $C_1$–$C_6$ group, for example a $C_1$–$C_4$ group.

Alkylidenedioxy represents a divalent organic group of general formula: —O-A-O—, where A denotes optionally substituted alkylene, as defined above.

A particularly preferred example of an arylalkyl group is benzyl.

An example of an triarylalkyl group is trityl.

The substituents of the aryl and heteroaryl groups are generally selected from halogen atoms and the following groups: nitro; optionally halogenated ($C_1$–$C_{14}$)alkoxy (and preferably trifluoromethoxy); ($C_1$–$C_{14}$)thioalkoxy which is optionally halogenated, preferably ($C_1$–$C_{10}$)thioalkoxy; optionally halogenated, preferably perhalogenated, ($C_1$–$C_{14}$)alkyl (and in particular methyl or trifluoromethyl); ($C_1$–$C_{14}$)alkylcarbonyl in which the alkyl part is optionally halogenated; ($C_6$–$C_{18}$)arylcarbonyl in which the aryl part is optionally substituted one or more times by halogen, optionally halogenated ($C_1$–$C_{14}$)alkyl and/or optionally halogenated ($C_1$–$C_{14}$)alkoxy; ($C_1$–$C_{14}$)alkylcarbonylamino in which the alkyl part is optionally halogenated; ($C_6$–$C_{18}$) arylcarbonylamino in which aryl is optionally substituted one or more times by halogen, optionally halogenated ($C_1$–$C_{14}$)alkyl and optionally halogenated ($C_1$–$C_{14}$)alkoxy; and ($C_6$–$C_{18}$)aryl optionally substituted one or more times by halogen, optionally halogenated ($C_1$–$C_{14}$)alkyl, such as trifluoromethyl, and optionally halogenated ($C_1$–$C_{14}$) alkoxy, such as trifluoromethoxy.

The term "halogen atom" is understood to mean a chlorine, bromine, iodine or fluorine atom.

The aryl and heteroaryl groups can be substituted by one or more of the substituents listed above, preferably one to three times, for example one to two times.

The alkyl groups and the alkyl parts of the abovementioned radicals and the alkylene radicals or the alkylene parts of the abovementioned radicals can be substituted one or more times by one or more radicals independently selected from halogen, such as bromine, ($C_1$–$C_{14}$)alkoxy or ($C_1$–$C_{14}$) thioalkoxy, preferably by one to three radicals of this type.

When one of $R^1$ and/or $R^2$ represents substituted amino, the substituents can be an optionally substituted alkyl group, an optionally substituted aryl group, an optionally substituted heteroaryl group, an optionally substituted arylalkyl group or an optionally substituted heteroarylalkyl group.

When, in the disaccharides of formula I, $R^1$ and/or $R^2$ represent a protected hydroxyl group, it is preferable for the latter to be selected from benzyloxy which is optionally substituted; allyloxy; trityloxy; tetrahydropyranyloxy; 3-bromotetrahydropyranyloxy; tetrahydrothiopyranyloxy; 1-methoxycyclohexyloxy; 4-methoxytetrahydropyranyloxy; 4-methoxytetrahydrothiopryanyloxy; acetoxy; 2-haloacetoxy; an —O—SiR$^f$R$^g$R$^h$ group where R$^f$, R$^g$ and R$^h$ are either all three identical or different alkyls or all three identical or different aryls; tosyloxy; and mesyloxy.

The compounds of formula I can be prepared in several stages. The process of synthesis comprises first of all the reaction of hydrogen fluoride with a compound of formula II:

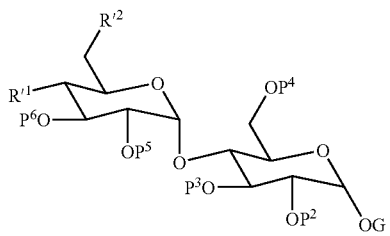

(II)

in which:
P², P³, P⁴, P⁵ and P⁶ are protective groups for hydroxyl functional groups;
R'¹ and R'² respectively denote R¹ and R² or else are precursor groups of the R¹ and R² substituents; and
G represents a group which can be displaced by a fluoride ion, such as an alkylcarbonyl group, where alkyl is as defined above; an allyl group; a 1,2-epoxide group or a —C(=NH)—CCl₃ group; or else G and P² together form an alkylidenedioxy group as defined above.

Preferably, G represents an acetyl group, it being possible for the P², P³, P⁴, P⁵ and P⁶ groups to be identical.

In an alternative form, it is possible to envisage the reaction of hydrogen fluoride with a compound of formula II:

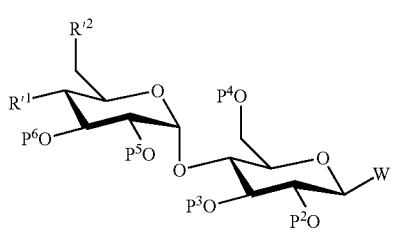

(II')

in which:
R'¹, R'², P², P³, P⁴, P⁵ and P⁶ are as defined above for the formula II and W represents SG, SeG or TeG, G being as defined above, it being understood that G and P² can together form an alkylene chain, where alkylene is as defined above.

This reaction can be carried out in the absence of solvent and in the presence of a large excess of hydrogen fluoride, the latter acting as solvent.

However, the reaction is advantageously carried out in a solvent, such as pyridine. More preferably, the reaction is additionally carried out in the presence of a large excess of hydrogen fluoride.

Thus, according to a preferred embodiment of the invention, the compound of formula II above is dissolved in a 10/1 to 1/1 hydrogen fluoride/pyridine mixture. This reaction is usually carried out at ambient temperature and more generally at a temperature of between −10 and 50° C., for example of between 15 and 30° C.

According to a preferred embodiment of the invention, P², P³, P⁴, P⁵ and P⁶ represent alkylcarbonyl groups, such as acetyl groups, R'¹ represents a hydroxyl group and R'² is selected from a halogen atom (such as a bromine atom) or an alkylcarbonyl group, such as an acetyl group.

The compound obtained on conclusion of this first stage has the formula:

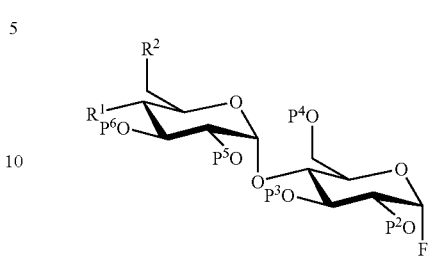

III in which P², P³, P⁴, P⁵, P⁶, R'¹ and R'² are as defined above for the formula III.

The following stages, resulting in the isolation of the compound of formula I, will be easily adjusted by a person skilled in the art according to the nature of the R¹ and R² groups in the targeted compound of formula These stages comprise, in any order, (i) the deprotection of the hydroxyl functional groups respectively protected by P², P³, P⁴, P⁵ and P⁶ and, if appropriate, (ii) the conversion of R'¹ and R'² groups to R¹ and R² groups.

When, in the compounds of formula II, R'¹ represents a hydroxyl group and R'² is identical to the P², P³, P⁴, P⁵ and P⁶ groups (identical to one another), the conversion of the compound III to a compound of formula I comprises, for example:

a first stage of conversion of the hydroxyl group in the 4$^{II}$ position to the R¹ group;

the subsequent simultaneous deprotection of the hydroxyl groups in the 2$^I$, 3$^I$, 6$^I$, 2$^{II}$, 3$^{II}$ and 6$^{II}$ positions;

and, if appropriate, the conversion of the hydroxyl group in the 6$^{II}$ position to the R² group.

According to another of its aspects, the invention relates to the use of a disaccharide as defined above in transglycosylation reactions catalyzed by glycoside hydrolases or in transfer reactions catalyzed by transglycosylases. In these reactions, the disaccharides of the invention, substrates of the enzymes of glycoside hydrolase and/or transglycolase type, function as glycosyl donors.

According to a particularly preferred embodiment of the invention, the disaccharides of the invention are used as substrates of enzymes belonging to family 13 of the glycoside hydrolases. These enzymes include in particular α-amylases, pullulanases, cyclomaltodextrin glucanotransferases, cyclomaltodextrinases, oligo-α-glucosidases, maltogenic amylases, neopullulanases, α-glucosidases, maltotetraose-forming α-amylases, isoamylases, glucodextranases, maltohexaose-forming α-amylases, branching enzymes, 4-α-glucanotransferases, maltopentaose-forming α-amylases and amylosucrases.

In the context of the invention, said enzymes are used for the preparation of oligo- or polysaccharides by sequential condensation of glycosyls.

According to a particularly preferred embodiment of the invention, use is made, as enzyme substrate, of a disaccharide of formula I in which R² represents a halogen atom, and more particularly bromine, for the purpose of the preparation of branched oligosaccharides, that is to say of oligosaccharides in which the monosaccharide units form sequences with branchings.

It should be understood that, conversely, the term "linear oligosaccharides" is understood to mean, according to the invention, oligosaccharides in which the monosaccharide units form linear sequences.

In a more particularly preferred way, the preparation of oligo- and polysaccharides involves cyclodextrin glycosyltransferase (cGTase) as enzyme of glycoside hydrolase type.

According to another of its aspects, the invention relates to a process for the preparation of oligosaccharides or of polysaccharides comprising the reaction of at least one disaccharide of formula I of the invention with a glycosyl acceptor, in the presence of an enzyme of glycoside hydrolase type or of transglycosylase type.

According to a preferred embodiment of the invention, the synthesis of oligo- or polysaccharides from the disaccharides of the invention involves one or more condensation reactions between the unit of maltosyl type of a disaccharide of formula I and the pyranosyl unit of a glycosyl acceptor.

In fact, in a particularly advantageous way, the process of the invention comprises one or more coupling reactions between a disaccharide of the invention and a glycosyl acceptor exhibiting, at their non-reducing end, a pyranosyl unit carrying at least one functional group capable of reacting with said disaccharide of formula I, the glycoside bond occurring between this pyranosyl unit and the anomeric carbon carrying the fluorine atom of the disaccharide of the invention, which disaccharide functions as glycosyl donor.

Examples of preferred pyranosyl units are the allose, altrose, glucose, gulose, mannose, idose, galactose or talose units.

Preferably, the synthesis of the oligosaccharide or of the polysaccharide comprises a stage of condensation between the unit of maltosyl type of the disaccharide of the invention and the pyranosyl unit of the glycosyl acceptor, said condensation proceeding via the reaction of a single hydroxyl group of the pyranosyl unit of the glycosyl acceptor with the anomeric carbon of said unit of maltosyl type.

One of the advantages of the invention lies in the possibility of controlling, stage by stage, the synthesis of the oligosaccharide, respectively of the final polysaccharide.

It is sufficient, on conclusion of each stage of condensation with a disaccharide of the invention, to carry out a further condensation reaction, after possible deprotection of a hydroxyl functional group of the oligosaccharide obtained, which becomes the glycosyl acceptor for said further condensation reaction.

Preferably, the anomeric carbon carrying the fluorine of the disaccharide of the invention reacts with a hydroxyl, thiol or amine functional group (and more particularly a hydroxyl functional group) preferably situated in the 4 position of the pyranosyl unit of the glycosyl acceptor. More generally, this functional group of the pyranosyl unit is situated in the 2, 3, 4 or 6 position.

The glycosyl acceptor can, without distinction, be a monosaccharide, such as methyl α-D-glucopyranoside, an oligosaccharide or a polysaccharide, such as pullulan.

It is very particularly preferable for the glycosyl acceptor to be pullulan and for the disaccharide of the invention to be a disaccharide of formula I in which $R^1$=$NH_2$ or azido and $R^2$=OH or alternatively $R^1$ and $R^2$ independently represent $NH_2$ or azido.

The resulting polymer is especially particularly advantageous as a novel vector in gene therapy.

Thus, according to another of its aspects, the invention relates to a vector, which can be used in gene therapy, resulting from the condensation of a polysaccharide composed of a linear or branched sequence of glycopyranosyl units with one or more disaccharides of formula I as defined above, said condensation involving the reaction of one or more hydroxyl functional groups in the 4 position of the glycopyranosyl units of said polysaccharide with an anomeric carbon carrying the fluorine atom of said disaccharides of formula I.

Preferably, said polysaccharide is pullulan.

Preferably, the disaccharide of formula I is a disaccharide of formula I in which $R^1$ and $R^2$ independently represent $NH_2$ or azido; or alternatively $R^1$=$NH_2$ or azido; and $R^2$=OH.

More generally, the process of the invention is appropriate for branching, in a controlled way, the 4 positions of the monosaccharide units of pullulan.

Other examples, which can be used in the context of the invention, of a polysaccharide which is a glycosyl acceptor are in particular dextrans which may be linear or branched, alternans, amylose, glycogen, amylopectin and more generally any polysaccharide capable of being a glycosyl acceptor when a compound of type I as defined in the invention is used.

According to the invention, the coupling of the disaccharide of the invention with the glycosyl acceptor is carried out in an aqueous medium, at a pH in the region of neutrality, for example at a pH of between 6 and 8, preferably at pH 7.

The coupling is generally carried out in a buffered aqueous solution.

In an alternative form, the coupling can also be carried out by addition of an inorganic base, such as sodium hydroxide, the addition being carried out using an automatic burette controlled by a pH meter.

Examples of buffers which can be used for this purpose are phosphate, sulfate, acetate, citrate, succinate and maleate buffers, phosphate buffers being preferred.

The condensation is usually carried out by bringing together one equivalent of a glycosyl acceptor and 1 to 5 molar equivalents, preferably 1.2 to 3.5 equivalents, of the maltosyl fluoride derivative of formula I.

The enzyme functioning as catalyst is present in the reaction medium in a catalytic amount. Use is thus made of less than one equivalent of enzyme per one molar equivalent of glycosyl acceptor (generally, an amount of less than $10^{-3}$M, better still of less than $10^{-4}$M and, for example, of between $10^{-4}$ and $10^{-6}$M (such as an amount of the order of $10^{-5}$M) is usually sufficient).

The reaction is generally carried out at a temperature of less than 100° C.

There are many advantages to this type of synthesis of oligo- and polysaccharides using enzymes of glycoside hydrolase or transglycosylase type:
 the production costs are reduced;
 as the syntheses are carried out in an aqueous medium, the products obtained are devoid of residual organic solvents, which guarantees that they are completely harmless.

The invention is illustrated below by the following synthetic examples 1 to 6.

In the examples, PE denotes petroleum ether, MP the experimental melting point and $MP_{litt}$ the melting point reported in the literature.

EXAMPLE 1 a) Preparation of 2,3-di-O-acetyl-α-D-glucopyranosyl-(1→4)-1,2,3,6-tetra-O-acetyl-β-D-glucopyranose

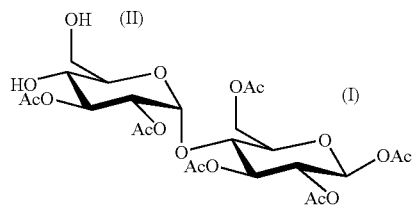

A1

A tetrafluoroboric acid solution (HBF$_4$/H$_2$O, 35% v/v, 6.1 ml) is added to a solution of peracetylated 4',6'-O-benzylidenemaltose (15 g, 22 mmol) in solution in acetonitrile (420 ml). The mixture is stirred at ambient temperature for 10 minutes, neutralized with triethylamine (6.8 ml) and then evaporated.

After purifying by fast chromatography (EtOAc 3/PE 1), the expected compound is crystallized from a dichloromethane/ether mixture (12 g, 92%).

MP=204–205° C. MP$_{litt}$=205–206° C.: K. Takeo and K. Shinmitsu, Carbohydr. Res., 133, 1984, 135–145. $^{13}$C NMR (300 MHz, CDCl$_3$): 171.08–168.8 (COCH$_3$); 95.82 (C1$^{II}$); 91.29 (C1$^I$); 75.21, 73.10, 72.78, 72.05, 71.92, 70.92, 70.28, 69.42 (C2$^1$, C3$^1$, C4$^1$, C5$^1$, C2$^{II}$, C3$^{II}$, C4$^{II}$, C5$^{II}$); 62.63 (C6$^I$); 61.87 (C6$^{II}$); 20.78–20.46 (COCH$_3$)

I and II refer respectively to the glycoside units represented in the formula A1 above.

b) Preparation of 2,3,6-tri-o-acetyl-α-D-glucopyranosyl-(1→4)-1,2,3,6-tetra-O-acetyl-β-D-glucopyranose

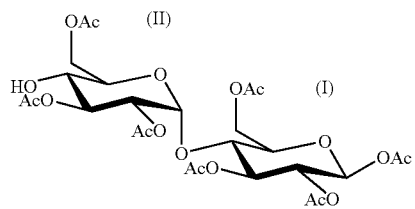

B1

The compound obtained in the preceding stage (6.075 g, M=594 g/mol), 10.2 mmol) and N-hydroxybenzotriazole acetate (2.004 g, 1.2 eq) are dissolved in dichloromethane (60 ml). Triethylamine (2.112 ml) is added. The reaction mixture is stirred at ambient temperature for 20 h. The solvent is evaporated. The expected compound is obtained by crystallization from ethyl ether (5.164 g, 80%).

$^1$H NMR (3.00 MHz, CDCl$_3$): 5.64 (H1$^I$; d; J$_{1,2}$=8.4 Hz); 5.22 (H1$^{II}$; d; J$_{1,2}$=3.66 Hz); 5.17 (H3$^I$; t; J$_{2,3}$=J$_{3,4}$=8.4 Hz); 5.1 (H3$^{II}$; t; J$_{2,3}$=10.2 Hz; J$_{3,4}$=9.8 Hz); 4.84 (H2$^I$; t; J$_{1,2}$=J$_{2,3}$=8.4 Hz); 4.66 (H2$^{II}$; dd; J$_{1,2}$=3.66 Hz; J$_{2,3}$=10.23 Hz); 4.37 (H6a$^I$; dd; J$_{5,6a}$≠2 Hz; J$_{6a,6b}$≠12 Hz); 4.34 (H6a$^{II}$; dd; J$_{5,6a}$=4.02 Hz; J$_{6a,6b}$=12.06 Hz); 4.14 (H6b$^{II}$); 4.10 (H6b$^I$); 3.9 (H4$^I$; t; J$_{4,5}$=J$_{3,4}$=8.4 Hz); 3.73 (H5$^I$); 3.69 (H5$^{II}$); 3.45 (H4$^{II}$; t; J$_{4,5}$=J$_{3,4}$=9.8 Hz); 2.01, 2.0, 1.98, 1.93, 1.89 (CH$_3$CO; s; 21 H); $^{13}$C NMR (300 MHz, CDCl$_3$): 171.06, 170.62, 170.52, 170.37, 169.88, 169,41, 168.65 (COCH$_3$); 95.75 (C1$^{II}$); 91.09 (C1$^I$); 74.94, 72.88, 72.31, 71.46, 70.84, 70.77, 70.03, 68.47 (C2$^1$, C3$^1$, C4$^1$, C5$^1$, C2$^{II}$, C3$^{II}$, C4$^{II}$, C5$^{II}$) 62.37 (C6$^I$, C6$^{II}$); 20.53–20.26 (COCH$_3$)

I and II refer respectively to the glycoside units represented in the formula B1.

Elemental analysis C$_{26}$H$_{36}$O$_{18}$: Calc. C=49.06%; H=5.7%. Found C=48.97%; H=5.85% c) Preparation of 2,3,6-tri-O-acetyl-α-D-glucopyranosyl-(1→4)-2,3,6-tri-O-acetyl-α-D-glucopyranosyl fluoride

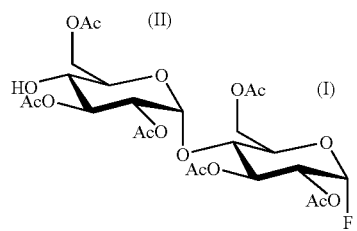

C1

The reaction is carried out at 0° C. in a plastic container.

The heptaacetate obtained in the preceding stage (5 g, 7.86 mmol) is dissolved in a solution of hydrogen fluoride in pyridine (7:3, v/v, 30 ml). After stirring for half an hour, the reaction mixture is diluted with dichloromethane and then poured onto an ice-cold 3 M aqueous ammonia solution.

After separation by settling, the organic phase is washed twice with an ice-cold saturated sodium hydrogencarbonate solution. The organic phase is subsequently dried over anhydrous sodium sulfate and then evaporated using a rotary evaporator.

Fast chromatography (EtOAc 2/PE 1) using a silica gel neutralized beforehand with triethylamine makes it possible to obtain the expected fluoride (4.45 g, 95%).

$^1$H NMR (300 MHz, CDCl$_3$): 5.6 (H1; dd; JH$_{1,2}$=2.56 Hz; J$_{H,F}$=54 Hz); 5.48 (H3$^I$; dd#t; J$_{3,4}$#9.5 Hz); 5.33 (H1$^{II}$; d; JH$_{1,2}$=4.0 Hz); 5.17 (H3$^{II}$; dd#t; J$_{3,4}$=10.1 Hz); 4.79 (H2$^I$; ddd; J$_{1,2}$=2.56; J$_{2,3}$=10.05 Hz; J$_{H,F}$=22.5 Hz); 4.75 (H2$^{II}$; dd; J$_{1,2}$=4.0 Hz; J$_{2,3}$=10.6 Hz); 4.5 (H6a$^I$; dd; J$_{5,6a}$=2 Hz; J$_{6a,6b}$=12.4); 4.41 (H6a$^{II}$; dd; J$_{5,6a}$=3.6 Hz; J$_{6a,6b}$=12.4 Hz); 4.18 (H6b$^I$; H6b$^{II}$); 4.11 (H5$^I$; m); 3.99 (H4$^I$; t; J$_{4,5}$=9.3 Hz); 3.75 (H5$^{II}$; m); 3.5 (H4$^{II}$; dt; JH$_{4,5}$ # 10.1 Hz; J$_{H, OH}$=5.6 Hz); 3.21 (nonbonded OH, J$_{OH, H}$=5.6 Hz); 2.1, 2.08, 2.04, 2.02, 1.97 (21 H, COCH$_3$). $^{13}$C NMR (300 MHz, CDCl$_3$): 171.33–169.69 (COCH$_3$); 103.56 (C1$^I$; d; J$_{C, F}$=229.3 Hz); 95.84 (C1$^{II}$); 71.81, 71.66, 71.58, 71.21, 70.72, 70.30, 69.99, 68.69 (C2$^1$, C3$^1$, C4$^1$, C5$^1$, C2$^{II}$, C3$^{II}$, C4$^{II}$, C5$^{II}$); 62.36, 62.12 (C6$^I$, C6$^{II}$); 20.71–20.41 (COCH$_3$) M.S. (FAB): m/z=659 Da [M+Na]$^+$ Elemental analysis C$_{24}$H$_{33}$FO$_{16}$: Calc.: C, 48.32; H=5.58; F, 3.18. Found: C, 48.34; H=5.82; F, 2.98.

I and II refer respectively to the glycoside units represented in the formula C1 above.

d) Preparation of 2,3,6-tri-O-acetyl-4-O-tetrahydropyranyl-α-D-glucopyranosyl-(1→4)-2,3,6-tri-O-acetyl-α-D-glucopyranosyl fluoride

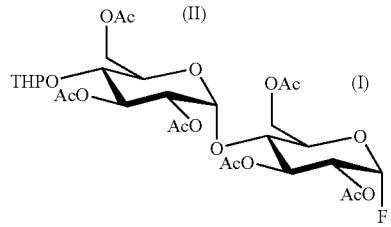

The compound obtained in the preceding stage (3 g, 5 mmol) is dissolved in distilled dichloromethane (120 ml). Dihydropyran (2.3 ml) is added, along with camphorsulfonic acid (86 mg). After stirring at ambient temperature for 3 h, the reaction mixture is washed with a saturated sodium hydrogencarbonate solution. The organic phase is dried over anhydrous sodium sulfate and then evaporated. After purifying by fast chromatography (EtOAc 1/PE 1) using a silica gel neutralized beforehand with triethylamine, the expected compound is obtained in the form of a mixture of diastereoisomers (3.420 g; 98%).

$^1$H NMR (300 MHz, CDCl$_3$): no interpretation, mixture of diastereoisomers. $^{13}$C NMR (300 MHz, CDCl$_3$): 170.54–169.31 (COCH$_3$), 103.56 (C1$^I$; d; J$_{C,F}$=229.3 Hz); 102.05, 101.62 (R and S acetal C of the tetrahydropyran), 95.72 (C1$^{II}$); 75.28, 73.59, 71.75, 71.68, 71.48, 70.77, 70.43, 70.38, 70.26, 69.99, 69.84, 69.74 (C2$^I$, C3$^I$, C4$^I$, C5$^I$, C2$^{II}$, C3$^{II}$, C4$^{II}$, C5$^{II}$); 64.03, 63.34, 62.61, 62.14, 62.1, 62.02 (R and S C6$^{II}$, C6$^I$, R and S tetrahydropyranyl C); 31.07–24.99 (tetrahydropyranyl); 20.76–20.41 (COCH$_3$); 20.09, 19.67 (1 R and S tetrahydropyranyl C). Elemental analysis: Calc.: C, 51.18; H, 6.07; F, 2.79. Found: C, 51.19; H, 6.15. M.S. (DCI): m/z=698 Da [M+NH$_4$]$^+$ I and II refer respectively to the glycoside units represented in the formula D1 above.

e) Preparation of 4-0-tetrahydropyranyl-α-D-glucopyranosyl-(1→4)-α-D-glucopyranosyl fluoride

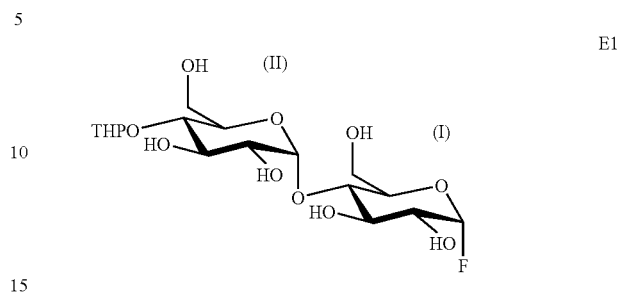

The peracetylated compound obtained in the preceding stage (1.55 g, 2.28 mmol) is dissolved in methanol (50 ml). A solution of sodium methoxide in methanol (1M, 2.5 ml) is added. After stirring at ambient temperature for 30 minutes, the reaction mixture is cooled to 0° C. and then neutralized with Amberlite IRN 120 H$^+$ resin. After filtration, the compound is concentrated and the residue is taken up in water and lyophilized (956 mg, 2.23 mmol). This compound is used without further purification.

This fluoride is stable at −18° C. in the lyophilized form.

Note: the first decomposition compound is α-maltosyl fluoride.

M.S. (FAB): m/z=429 Da [M+H]$^+$

EXAMPLE 2

Preparation of 2,3,4,6-tetra-O-acetyl-α-D-glucopyranosyl-(1→4)-2,3,6-tri-o-acetyl-α-D-glucopyranosyl-(1→4)-[2,3,4,6-tetra-O-acetyl-α-D-glucopyranosyl-(1→4)-2,3,6-tri-O-acetyl-α-D-glucopyranosyl-(1→4)-2,3,6-tri-O-acetyl-α-D-glucopyranosyl-(1→6)]-2,3-di-O-acetyl-α-D-glucopyranosyl-(1→4)-1,2,3,6-tetra-O-acetyl-D-glucopyranose

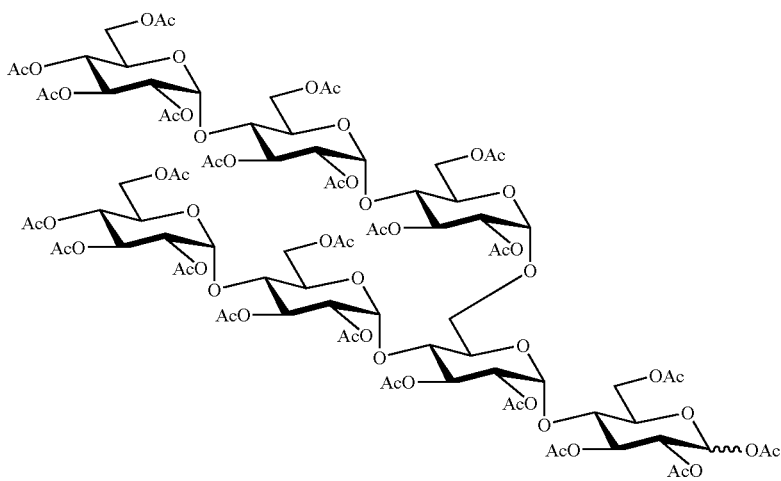

Panose (α-D-glucopyranosyl-(1→6)-α-D-glucopyranosyl-(1→4)-D-glucopyranose) (80 mg, 0.158 mmol) and modified maltosyl fluoride obtained in example 1e) (171 mg, 0.4 mmol, 2.5 eq) are dissolved in a phosphate buffer solution (8 ml, 0.1M, pH =7). cGTase (in a catalytic amount) is added. The mixture is stirred at ambient temperature for two hours. Thin layer chromatography (eluent H$_2$O 1/CH$_3$CN 2) shows that the fluoride has been completely converted. The reaction mixture is brought to 100° C. for 5 minutes. The protein is filtered off on a cotton filter. The filtrate is lyophilized and then acetylated in a pyridine/acetic anhydride mixture (1.5:1, v/v, 25 ml) overnight at 70° C. Methanol (10 ml) is added at 0° C. to neutralize the excess acetic anhydride. The reaction mixture is concentrated on a rotary evaporator, the residue is taken up in CH$_2$Cl$_2$ and the solution is washed with water and then with a saturated NaHCO$_3$ solution. The aqueous phases are extracted with CH$_2$Cl$_2$ (3 times). The organic phases are combined, dried over Na$_2$SO$_4$ and then evaporated to dryness. The residue is taken up in CH$_2$Cl$_2$ (10 ml) and trifluoroacetic acid (10 ml) is added. The reaction mixture is stirred at ambient temperature for 30 minutes and evaporated to dryness, and the residue is then acetylated in a pyridine/acetic anhydride mixture (1.5:1, v/v, 3.5 ml) at ambient temperature for 14 hours. The mixture is then cooled to 0° C. and methanol (1 ml) is added. After evaporating on a rotary evaporator, the residue is purified by fast chromatography (CH$_2$Cl$_2$ 100/MeOH 1), w=230 mg (0.125 mmol, 80%).

M.S. (electrospray) m/z=2141 (M+Na)$^+$

EXAMPLE 3

Preparation of α-D-glucopyranosyl-(1→4)-α-D-glucopyranosyl-(1→4)-[α-D-glucopyranosyl-(1→4)-α-D-glucopyranosyl-(1→4)-α-D-glucopyranosyl-(1→6)]-α-D-glucopyranosyl-(1→4)-D-glucopyranose coevaporated with water and then lyophilized to give the expected compound, 61 mg (96%).

High resolution M.S.: m/z=1191.3441 Da [M+K]$^+$ Corresponding to C$_{42}$H$_{72}$O$_{36}$K m/z=1175.3701 Da [M+Na]$^+$ Corresponding to C$_{42}$H$_{72}$O$_{36}$Na Abbreviation DP used for: degrees of polymerization (number of glucosyl units) Coupled mass spectrometry/mass spectrometry:

Daughter ions of (M+Na)$^+$:
1012.8 Da (DP6+Na)$^+$
850.6 Da (DP5+Na)$^+$
688.9 Da (DP4+Na)$^+$
526.9 Da (DP3+Na)$^+$
347.1 Da (DP2+Na)$^+$
203.2 Da (DP1+Na)$^+$ $^1$H NMR: (400 MHz, D$_2$O (4.65 ppm), 298 K) H$_1$ α14 (three unresolved peaks): 5.23 ppm, 5.19 ppm, 5.149 ppm, d, J$_{12}$=4 Hz, H$_{1\alpha}$: 5.073 ppm, J$_{12}$=3.6 Hz and 5.028 ppm, J$_{12}$=4 Hz, H$_1$ α16: 4.808 ppm, d, J$_{12}$=3.2 Hz, H$_{1\beta}$: 4.491 ppm, d, J$_{12}$=8 Hz, 3.9–3.4 ppm, unresolved peak, any proton not mentioned H$_4$ of the nonreducing units: 3.249 ppm, t, J$_{32}$=9.6 Hz H$_{2\beta}$: 3.114 ppm, t, J$_{32}$≈J$_{12}$ $^{13}$C NMR: (400 MHz, D$_2$O, 298 K) 100.38, 100.09 ppm: C1 of α14 bonds; 98.92 ppm: C1 of α16 bond; 96.09 ppm: C1β; 92.21 ppm: C1α; 79.139, 78.25, 78.06, 77.85, 77.73, 77.14, 77.00, 76.42,

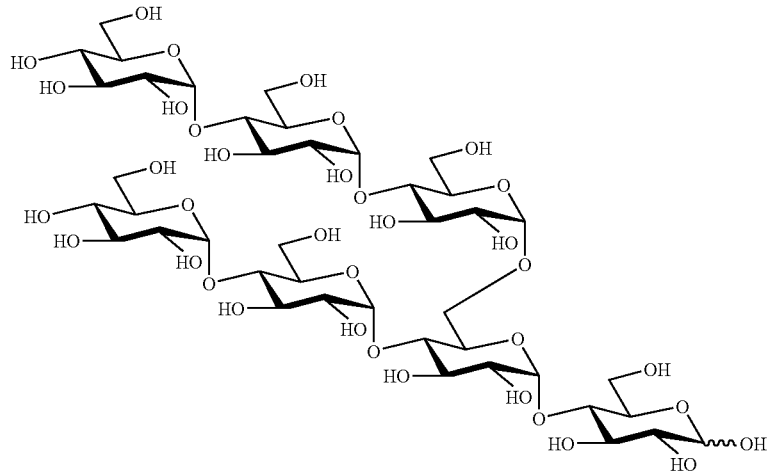

The compound of example 2 (100 mg, 0.546 mmol) is dissolved in MeOH (30 ml) and a solution of sodium methoxide in methanol is added (1M, 300 μl). The reaction mixture is stirred at ambient temperature overnight. Thin layer chromatography (H$_2$O 1/CH$_3$CN 1.5) reveals that the reaction is complete. The solution is subsequently neutralized with Amberlite IRN 120 (H$^+$) resin, evaporated, 74.98, 74.25, 73.70, 73.48, 73.30, 73.19, 73.05, 72.07, 71.98, 71.76, 71.62, 71.52, 70.65, 70.51, 70.38, 69.64 ppm: any carbon not mentioned (i.e. 28 carbons); 67.83–67.67: C6 belonging to the α16 glycoside bond; Splitting due: to the α form and to the β form or to the conformational equilibrium; 61.14, 60.90, 60.80, 60.67 ppm: C6 not participating in a glycoside bond (6 carbons).

EXAMPLE 4 a) Preparation of 2,3-di-O-acetyl-6-bromo-6-deoxy-α-D-glucopyranosyl-(1→4)-1,2,3,6-tetra-O-acetyl-β-D-glucopyranose

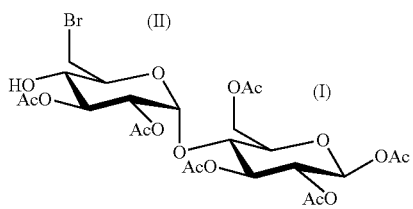

A4

Triphenylphosphine (PPh$_3$, 4 g, 2 eq) and carbon tetrabromide (CBr$_4$, 2.57 g, 1.02 eq) are added at 0° C. to a solution of the compound of example 1a) (5 g, 7.86 mmol) in pyridine (54 ml). The reaction mixture is stirred at 0° C. for 15 minutes and then at 50° C. for 3 hours. Thin layer chromatography (EtOAc 1/PE 1) shows that the starting material has disappeared. Methanol (5 ml) is then added. The reaction medium is evaporated and then coevaporated with toluene. The expected compound is obtained by purification by fast chromatography (4.2 g, 84%).

$^1$H NMR (300 MHz, CDCl$_3$): 5.68 (H1$^I$; d; J$_{1,2}$=8.22 Hz); 5.31 (H1$^{II}$, d, J$_{1,2}$=3.83 Hz); 5.24 (H3$^I$; t; J$_{3,4}$=8.7 Hz); 5.15 (H3$^{II}$; t; J$_{2,3}$≈J$_{3,4}$≈10.2 Hz); 4.84 (H2$^I$; t; J$_{2,3}$=9.14 Hz); 4.66 (H2$^{II}$; dd; J$_{2,3}$=10.3 Hz); 4.46 (H6a$^I$; dd; J$_{5,6a}$=2.4 Hz; J$_{6a,6b}$=12.2 Hz); 4.17 (H6b$^I$; dd; J$_{5,6a}$=4.7 Hz; J$_{6a,6b}$=12.2 Hz); 3.96 (H4$^I$; t; J$_{4,5}$=9.6 Hz); 3.79, 3.75 (H5$^I$; H5$^{II}$); 3.68–3.53 (H4$^{II}$; H6a$^{II}$; H6b$^{II}$; m); 2.06, 2.03, 2.02, 1.99, 1.96, 1.95 (CH$_3$CO; s; 18 H); $^{13}$C NMR (75 MHz, CDCl$_3$): 171.13–168.78 (COCH$_3$); 95.67 (C1$^I$); 91.18 (C1$^{II}$); 74.96, 73.12, 72.44, 71.73, 71.28, 70.82, 70.72, 70.14 (C2$^I$, C3$^I$, C4$^I$, C5$^I$, C2$^{II}$, C3$^{II}$, C4$^{II}$, C5$^{II}$); 62.61 (C6$^I$); 32.66 (C6$^{II}$); 20.75–20.38 (COCH$_3$). M.S. (DCI): m/z=674 Da (M+NH$_4$)$^+$

I and II refer to the glycoside units represented above in the formula A4.

b) Preparation of 2,3-di-O-acetyl-6-bromo-6-deoxy-α-D-glucopyranosyl-(1→4)-2,3,6-tri-O-acetyl-α-D-glucopyranosyl fluoride

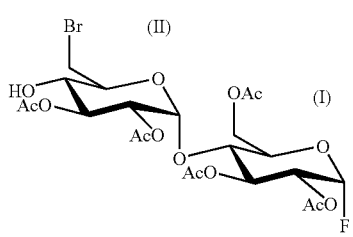

B4

The reaction is carried out at 0° C. in a plastic container.

The hexaacetate obtained in the preceding stage (2.041 g, 3.11 mmol) is dissolved in a solution of hydrogen fluoride in pyridine (7:3, v/v, 20 ml). After stirring for half an hour, the reaction mixture is diluted with dichloromethane and then poured onto an ice-cold 3M ammonia solution.

After separation by settling, the organic phase is washed twice with an ice-cold saturated sodium hydrogencarbonate solution. The organic phase is subsequently dried over anhydrous sodium sulfate and then evaporated using a rotary evaporator.

Fast chromatography (EtOAc 2/PE 1) using a silica gel neutralized beforehand with triethylamine makes it possible to obtain the expected fluoride (1.71 g, 90%).

$^1$H NMR (300 MHz, CDCl$_3$): 5.59 (H1; dd; JH$_{1,2}$=2.93 Hz; J$_{H,F}$=53.3 Hz); 5.47 (H3$^I$; dd; J$_{3,4}$=8.8 Hz); 5.34 (H1$^{II}$; d; JH$_{1,2}$=3.6 Hz); 5.15 (H3$^{II}$; dd; J$_{3,4}$=9.14 Hz); 4.76 (H2$^I$; ddd; J$_{2,3}$=10.23 Hz; J$_{H,F}$≈23 Hz); 4.73 (H2$^{II}$; dd; J$_{2,3}$=10.6 Hz); 4.51 (H6a$^I$; dd; J$_{5,6a}$=2.2 Hz; J$_{6a,6b}$=12.4); 4.17 (H6b$^I$; dd; J$_{5,6b}$=4.02 Hz); 4.10 (H5$^I$; m); 3.99 (H4$^I$; t; J$_{4,5}$≈9.8 Hz); 3.75 (H5$^{II}$; m); 3.6–3.48 (H4$^{II}$; H6a$^{II}$; H6b$^{II}$; m); 2.07, 2.02, 2.01, 2.0, 1.97, 1.96 (18 H, COCH$_3$). $^{13}$C NMR (75 MHz, CDCl$_3$): 171.33–169.76 (COCH$_3$); 103.54 (C1$^1$; d; J$_{C,F}$=227.8 Hz); 95.70 (C1$^{II}$); 71.80, 71.31, 70.7, 70.35, 70.06 (C2$^I$, C3$^I$, C4$^I$, C5$^I$, C2$^{II}$, C3$^{II}$, C4$^{II}$, C5$^{II}$); 62.17 (C6$^I$); 32.71 (C6$^{II}$); 20.9–20.36 (COCH$_3$)

I and II refer to the glycoside units represented above in the formula B4.

c) Preparation of 2,3-di-O-acetyl-6-bromo-6-deoxy-4-O-tetrahydropyranyl-α-D-glucopyranosyl-(1→4)-2,3,6-tri-O-acetyl-α-D-glucopyranosyl fluoride

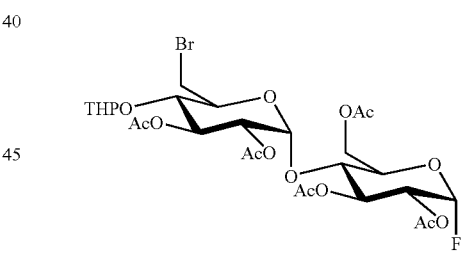

C4

The compound obtained in the preceding stage (1.725 g, 2.79 mmol) is dissolved in distilled dichloromethane (95 ml). Dihydropyran (1.4 ml) is added, along with camphorsulfonic acid (50 mg). The reaction mixture is stirred at ambient temperature for 2 hours and then washed with a saturated sodium hydrogencarbonate solution. The organic phase is dried over anhydrous sodium sulfate and then evaporated. After purification by fast chromatography (EtOAc 1/PE 1) using a silica gel neutralized beforehand with triethylamine, the expected compound is obtained in the form of a mixture of diastereoisomers (1.8 g, 95%).

NMR: no interpretation, mixture of diastereoisomers. M.S. (DCI): m/z=718 Da (M+NH$_4$)$^+$ d) Preparation of 6-bromo-6-deoxy-4-O-tetrahydropyranyl-α-D-glucopyranosyl-(1→4)-α-D-glucopyranosyl fluoride

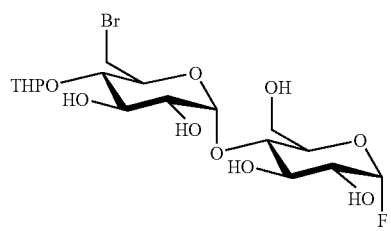

D4

The peracetylated compound obtained in the preceding stage (1 g, 1.42 mmol) is dissolved in methanol (20 ml). A solution of sodium methoxide in methanol (1M, 200 μl) is added. After stirring at ambient temperature for 30 minutes, the reaction mixture is cooled to 0° C. and then neutralized with Amberlite IRN 120 H$^+$ resin. After filtration, the compound is concentrated and the residue is taken up in water and lyophilized (683 mg, 98%).

This compound is used without additional purification. This fluoride is stable at −18° C. in the lyophilized form.

M.S. (FAB): m/z=513 Da (M+Na)$^+$

EXAMPLE 5

Preparation of methyl 2,3,4-tri-O-acetyl-6-bromo-6-deoxy-α-D-glucopyranosyl-(1→4)-2,3,6-tri-O-acetyl-α-D-glucopyranosyl-(1→4)-2,3,6-tri-O-acetyl-α-D-glucopyranoside

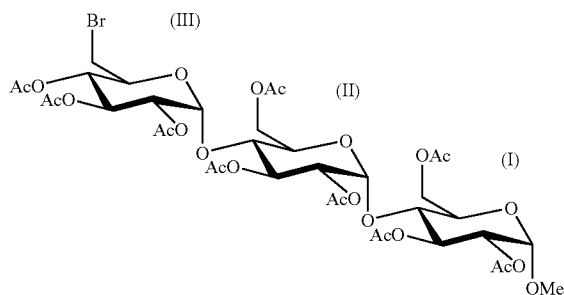

A5

The fluoride obtained in example 4d) (80 mg, 0.163 mmol) and methyl α-D-glucopyranoside (94.8 mg, 3 eq) are dissolved in a phosphate buffer solution (7 ml, 0.1M, pH=7.0). cGTase is added in a catalytic amount. The reaction mixture is incubated at 40° C. for 14 hours and is then heated at 100° C. for 5 minutes. The protein is filtered off through a cotton filter. The filtrate is acidified by addition of 50% acetic acid until a pH of approximately 4 is reached and is stirred for 1 hour. The mixture is subsequently neutralized by addition of a 10% ammonia solution and is then evaporated. The residue is coevaporated 3 times with water, is lyophilized and is then acetylated at 70° C. overnight in a pyridine/acetic anhydride mixture (1.5:1, v/v, 16 ml). Methanol (7 ml) is added at 0° C. to neutralize the excess acetic anhydride. The reaction mixture is concentrated on a rotary evaporator, the residue is taken up in $CH_2Cl_2$ and the solution is washed with water and then with a saturated $NaHCO_3$ solution. The aqueous phases are extracted with $CH_2Cl_2$ (3 times). The organic phases are combined and dried over $Na_2SO_4$.

The expected compound is obtained by fast chromatography (eluent: ethyl ether) (118 mg, 75%).

$^1$H NMR (300 MHz, CDCl$_3$): 5.48 (H3$^I$; dd; J$_{2,3}$=10.1 Hz; J$_{3,4}$=8.17 Hz); 5.38 (H1$^{III}$; d; J$_{1,2}$=3.9 Hz); 5.37 (H3$^{II}$; dd≠t*; J$_{3,4}$=8.32 Hz); 5.32 (H3$^{III}$; dd; J$_{3,4}$=9.61 Hz); 5.25 (H1$^{II}$; d; J$_{1,2}$=4.08 Hz); 4.98 (H4$^{III}$; dd ≠t*; J$_{3,4}$=9.04 Hz); 4.79 (H1$^I$; d; J$_{1,2}$=3.5 Hz); 4.79 (H2$^{III}$; dd; J$_{2,3}$=10.4 Hz); 4.72 (H2$^I$; dd; J$_{2,3}$=10.1 Hz); 4.70 (H2$^{II}$; dd; J$_{2,3}$=10.5 Hz); 4.45; 4.41 (H6a$^I$; H6a$^{II}$; dd; J$_{5,6a}$=2.5 Hz; J$_{6a,6b}$=12.24); 4.28; 4.19 (H6b$^I$; H6b$^{II}$; dd; J$_{5,6b}$=3.5 and 3.2 Hz); 3.9 unresolved peak (H4$^{II}$; H4$^{II}$; H5$^I$; H5$^{II}$; H5$^{III}$; 5H) 3.38 (CH$_3$; s); 3.38 +/−0.05 ppm unresolved peak (H6a$^{III}$; H6b$^{III}$); 2.13–1.94 (27 H, COCH$_3$). $^{13}$C NMR (300 MHz, CDCl$_3$): 171.2–168.7 (COCH$_3$); 96.58 (C1$^I$); 95.57, 95.42 (C1$^{II}$, C1$^{III}$); 73.72, 72.86 (C4$^I$, C4$^{II}$); 72.56 (C3$^I$); 71.58 (C3$^{II}$); 71.23 (C2$^I$); 70.53 (C4$^{III}$); 70.34, 70.12 (C2$^{II}$, C2$^{III}$); 69.09, 69.04, 68.98, 67.52 (C5$^I$, C5$^{II}$, C3$^{III}$, C5$^{III}$); 62.96, 62.53 (C6$^I$, C6$^{II}$); 55.27 (CH$_3$); 31.15 (C6$^{III}$); 21–20.38 (COCH$_3$)

(* dd≠t: double doublet virtually a triplet).

I, II and III refer to the glycoside units represented above in the formula A5.

M.S. (FAB): m/z=983 (M+Na)$^+$

EXAMPLE 6

Preparation of a Pullulan Modified by Condensation of Maltosyl Units at the 4 Positions of the Glycoside Units Stage a)

Pullulan (50 mg) and the fluoride obtained in example 1e) (63.4 mg, 1.5 eq) are dissolved in phosphate buffer (5 ml, 0.1M, pH=7.0). cGTase (in a catalytic amount) is added. The reaction mixture is incubated at ambient temperature for 2 hours. Thin layer chromatography (CH$_3$CN 4/H$_2$O 1) reveals that the fluoride has been completely converted. The reaction mixture is precipitated from 200 ml of ethanol (95%). The precipitate is recovered by centrifuging and is dried overnight under vacuum. 65 mg are thus obtained, i.e. a degree of substitution of approximately 37%.

Stage b)

The polymer obtained in the preceding stage (21 mg) is dissolved in a 10$^{-2}$M hydrochloric acid solution (2 ml). The reaction mixture is stirred at ambient temperature for 2 hours. The mixture is subsequently neutralized by addition of ammonia and is then precipitated from ethanol. After centrifuging, the polymer is dried under vacuum. 15 mg are thus isolated.

The degree of substitution is determined by methylation according to the Hakomori method.

The methylated polymer thus obtained is hydrolyzed in an acidic medium. The monosaccharides obtained are reduced and then acetylated. The mixture obtained is analyzed by coupled gas chromatography/mass spectrometry.

Glycosylated units: Area of 1-O-acetyl-2,3,4,6-tetra-O-methylhexytol: 17190

Non-glycosylated units: Area of 1,6-di-O-acetyl-2,3,6-tri-O-methylhexytol: 29163 Degree of substitution: 37%

The $^1$H NMR spectra of the polymers of examples 6a) and 6b) are compared with that of pullulan.

pectrum of pullulan: H$_1$ α14 (2 peaks): 5.27; 5.23 ppm; int*=2;
H$_1$ α16: 4.83 ppm; int*=1;
3.9–3.4 ppm; unresolved peak; any proton not mentioned: theoretical integral: 18
integral measured: 18.5

Polymer of example 5a): H$_1$ α14 (2 peaks): 5.26; 5.24 ppm; int*=2.56;
H$_1$ α16 (unresolved peak): 4.83 ppm; int*=1;
3.9–3.4 ppm; unresolved peak; any proton not mentioned;
1.71, 1.42 ppm; 2 peaks, int*=1.66,
tetrahydropyranyl group Polymer of example 5b): H$_1$ α14 (2 peaks): 5.26; 5.24 ppm; int*=2.56;
H$_1$ α16 (unresolved peak): 4.83 ppm; int*=1;
3.9–3.4 ppm; unresolved peak; any proton not mentioned;
1.71, 1.42 ppm; 2 peaks, int*=1.66

* result of the integration

EXAMPLE 7 a) Preparation of triphenylmethyl(2,3,6-tri-O-acetyl-4-O-tetrahydropyranyl-α-D-glucopyranosyl)-(1→4)-S-(2,3,6-tri-O-acetyl-α-glucopyranosyl)-(1→4)-2,3,6-tri-O-acetyl-thio-α-D-glucopyranoside

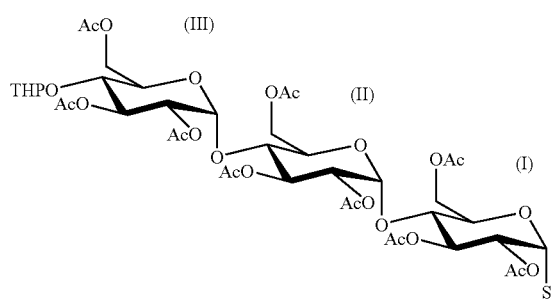

A7 cGTase (207 μl) is added to a solution of the fluoride E1 prepared in example 1e) (50 mg, 0.12 mmol) and triphenylmethyl thio-α-D-glucopyranoside (62 mg, 1.2 eq) in phosphate buffer (3 ml, 0.1M, pH=7.0). The reaction mixture is incubated at 40° C. for 2 hours, lyophilized and taken up in a pyridine/acetic anhydride mixture (10 ml, 1/1, v/v) and a catalytic amount of DMAP is added. The mixture is stirred at 70° C. for 12 hours, neutralized under cold conditions by addition of methanol at 0° C. (5 ml) and evaporated. The residue is taken up in dichloromethane and washed with water and then with a saturated sodium hydrogencarbonate solution. The organic phase is recovered, dried over anhydrous sodium sulfate, evaporated and coevaporated with toluene. The mixture of diastereoisomers is purified by fast chromatography (PE 1/EtOAc 1) (127 mg, 86%).

High resolution M.S. (ES+): C$_{60}$H$_{72}$O$_{25}$NaS [M+Na]$^+$ Calc.: m/z=1247.3981. Found: m/z=1247.3989. $^{13}$C NMR (75 MHz, CDCl$_3$): 170.69, 170.59, 170.32, 169.78, 169.49, 169.39, 169.32, 169.20 (COCH$_3$); 144.35 (aromatic C$^{IV}$); 129.79, 127.80, 126.94 (aromatic CH); 101.14, 100.67 (R and S acetal C of the tetrahydropyran); 95.77, 95.65 (C1$^{II}$, C1$^{III}$) 81.66 (C1$^I$); 76.58, 75.28, 73.93, 73.57, 72.59, 72.42, 71.78, 71.56, 70.36, 70.26, 69.79, 69.60, 69.25, 68.76 (C2$^I$, C3$^I$, C4$^I$, C5$^I$, C2$^{II}$, C3$^{II}$, C4$^{II}$, C5$^{II}$, C2$^{III}$, C3$^{III}$, C4$^{III}$, C5$^{III}$, CPh$_3$); 63.91, 63.20, 63.00, 62.54, 62.24, 62.00 (R and S C6$^{III}$, C6$^{II}$, C6$^I$, R and S tetrahydropyranyl C); 31.05, 30.92, 25.04, 24.92 (2 R and S tetrahydropyranyl C); 20.85, 20.75, 20.66, 20.51, 20.46 (COCH$_3$); 20.16, 19.53 (1 R and S tetrahydropyranyl C).

b) Preparation of (2,3,4,6-tetra-O-acetyl-α-D-glucopyranosyl)-(1→4)-(2,3,6-tri-O-acetyl-α-D-glucopyranosyl)-(1→4)-2,3,6-tri-O-acetyl-1-S-acetyl-1-thio-α-D-glucopyranose

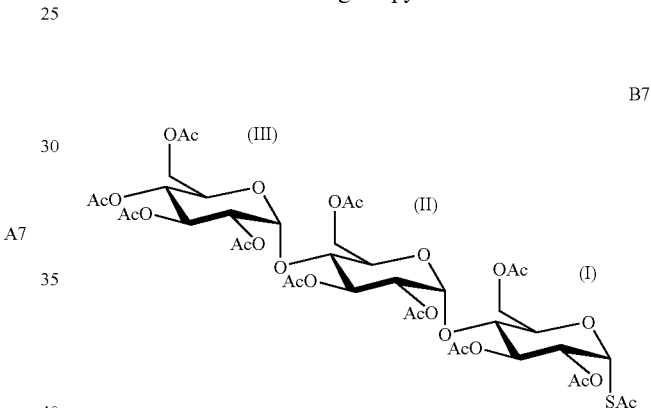

B7

Triethylsilane (Et$_3$SiH, 35.8 μl, 225 μmol) and trifluoroacetic acid (1.2 ml) are added to the compound A7 prepared in the preceding stage (81 mg, 66.2 μmol) dissolved in dichloromethane (1.9 ml). The mixture is stirred at ambient temperature for 45 minutes and is then evaporated. The residue is taken up in anhydrous pyridine (2 ml), and acetic anhydride (1.5 ml) and a catalytic amount of DMAP are added. The reaction mixture is stirred at ambient temperature for 12 hours, it is then neutralized by addition of methanol (1.2 ml) at 0° C. and is evaporated. The expected compound is purified by fast chromatography (PE/EtOAc: 1/1.5) (45 mg, 69%).

[α]$_D$: +183° (c=0.27, chloroform) High resolution M.S. (ES+): C$_{40}$H$_{54}$O$_{26}$SNa [M+Na]$^+$ Calc.: m/z=1005.2522. Found: m/z=1005.2519. $^1$H NMR (400 MHz, CDCl$_3$):

| B7 | Chemical shifts | | | | | | | Coupling constants | | | | | | |
| --- | --- | --- | --- | --- | --- | --- | --- | --- | --- | --- | --- | --- | --- | --- |
| | H1 | H2 | H3 | H4 | H5 | H6a | H6b | J12 | J23 | J34 | J45 | J5a | Jab | J5b |
| Unit I | 6.09 | 5.07 | 5.13 | 3.87 | 3.95 | 4.35 | 4.23 | 5.1 | 10.3 | 7 | 9.7 | 2.6 | 12.4 | 4.1 |
| Unit II | 5.22 | 4.72 | 5.35 | 3.9 | 3.94 | 4.42 | 4.13 | 4.1 | 10.3 | 9.6 | 9.6 | 2.2 | 12.3 | 3 |
| Unit III | 5.34 | 4.82 | 5.32 | 5.03 | 3.9 | 4.21 | 4.01 | 3.4 | 10.4 | 9.7 | 9.7 | 3.6 | 12.2 | 2.3 |

SCOC$\underline{H}_3$: 2.40 COC$\underline{H}_3$: 2.14, 2.12, 2.11, 2.06, 2.02, 2.00, 1.99, 1.97, 1.96 $^{13}$C NMR (100 MHz, CDCl$_3$):

| B7 | Chemical shifts | | | | | |
|---|---|---|---|---|---|---|
| | C1 | C2 | C3 | C4 | C5 | C6 |
| Unit I | 79.75 | 69.41 | 72.71 | 71.76 | 68.94 | 62.88 |
| Unit II | 96.02 | 70.34 | 71.76 | 68.47 | 72.47 | 62.23 |
| Unit III | 95.65 | 70.04 | 69.34 | 67.86 | 73.84 | 61.32 |

S$\underline{C}$OCH$_3$: 191.51     SCOC$\underline{H}_3$: 31.24
$\underline{C}$OCH$_3$: 170.3–169.2     COC$\underline{H}_3$: 20.41

EXAMPLE 8 a) Preparation of (2,3,4,6-tetra-O-acetyl-α-D-glucopyranosyl)-(1→4)-(2,3,6-tri-O-acetyl-α-D-glucopyranosyl)-(1→4)-(2,3-di-O-acetyl-6-bromo-6-deoxy-α-D-glucopyranosyl)-(1→4)-1,2,3,6-tetra-O-acetyl-D-glucopyranose The fluoride E1 prepared in example 1e) (250 mg, 0.58 mmol) and 6-bromo-6-deoxy-α-D-glucopyranosyl-D-glucopyranose (235 mg, 1 eq) are dissolved in phosphate buffer (25 ml, 0.1M, pH=7.0). cGTase (750 µl) is added and the reaction mixture is incubated at 40° C. for 1 hour and is then heated at 100° C. for 5 minutes. The enzyme is filtered off through a cotton filter. The filtrate is acidified by addition of hydrochloric acid until a pH of approximately 2 is reached and is stirred at room temperature for 20 minutes. The solution is then neutralized by addition of ammonia and is then lyophilized. The lyophilisate is dissolved in anhydrous pyridine (30 ml), and acetic anhydride (20 ml) and DMAP (<1 mg) are added. The reaction mixture is stirred at 70° C. for 12 hours and then the excess anhydride is neutralized by addition of methanol (20 ml) at 0° C. The reaction mixture is concentrated on a rotary evaporator, the residue is taken up in dichloromethane and the solution is washed with water and then with a saturated NaHCO$_3$ solution. The aqueous phases are extracted with dichloromethane (3 times). The organic phases are combined, dried over anhydrous potassium sulfate and evaporated.

The expected anomeric mixture is purified by fast chromatography (PE/EtOAc: 3/4) (521 mg, 70%).

M.S. (FAB+): m/z=1299 [M+Na]$^+$ Elemental analyses for C$_{24}$H$_{33}$BrO$_{16}$: Calc.: C, 47.07; H, 5.29; Br, 6.26. Found: C, 47.25; H, 5.52; Br, 6.34. $^1$H NMR (300 MHz, CDCl$_3$, 303° K): 6.62 (H1$^{I\alpha}$; d, J$_{1,2}$=3.7 Hz); 5.69 (H1$^{I\beta}$; d, J$_{1,2}$=8.0 Hz); 6.01, 3.70 (sugar H); 2.15, 1.93 (39 H, COCH$_3$) $^{13}$C NMR (75 MHz, CDCl$_3$, 303° K.): 170.56, 170.45, 170.34, 169.88, ($\underline{C}$OCH$_3$); 96.01, 95.64 (C1$^{II}$, C1$^{III}$, C1$^{IV}$); 91.21 (C1$^{I\beta}$); 88.81 (C1$^{I\alpha}$); 75.1, 74.56, 73.63, 73.51, 72.89, 72.40, 72.15, 71.73, 70.99, 70.40, 70.15, 69.97, 69.71, 69.39, 69.18, 68.96, 68.47, 68.01 (C2$^{I}$, C3$^{I}$, C4$^{I}$, C5$^{I}$, C2$^{II}$, C3$^{II}$, C4$^{II}$, C5$^{II}$, C2$^{III}$, C3$^{III}$, C4$^{III}$, C5$^{III}$, C2$^{IV}$, C3$^{IV}$, C4$^{IV}$, C5$^{IV}$); 62.72, 61.38 (C6$^{I}$, C6$^{III}$, C6$^{IV}$); 33.38 (C6$^{II}$); 20.77–20.48 (COC$\underline{H}_3$).

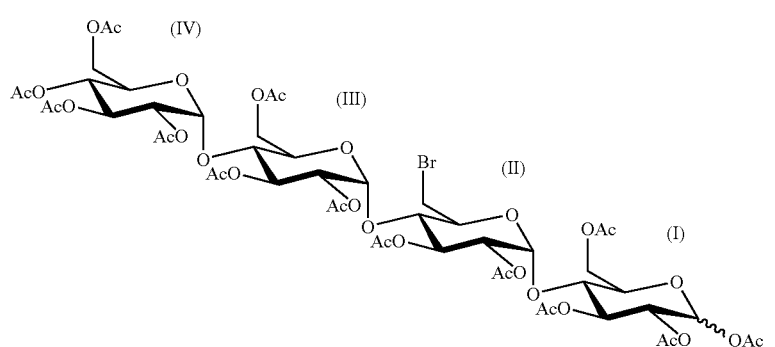

A8

EXAMPLE 9 a) Preparation of α-D-glucopyranosyl-(1→4-α-D-glucopyranosyl-(1→4) -[α-D-glucopyranosyl-(1→4)-α-D-glucopyranosyl-(1→4)-S-α-D-glucopyranosyl-(1→6)]-6-thio-α-D-glucopyranosly-(1→4)-D-glucopyranose

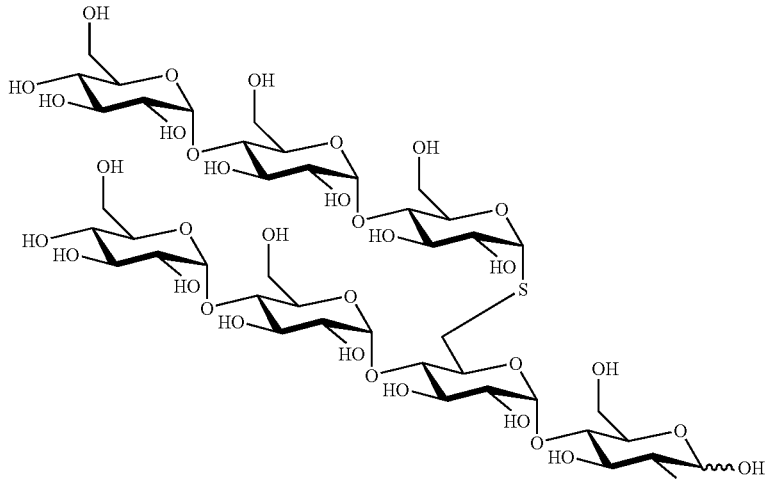

A9

S-α-D-Glucopyranosyl-(1→6)-6-thio-α-D-glucopyranosyl-(1→4)-D-glucopyranose (34.2 mg, 65.7 μmol) and the fluoride E1 prepared in example 1e) (94 mg, 4 eq) are dissolved in phosphate buffer (4.6 ml, 0.1M, pH=7.0). cGTase (141 μl) is added. The reaction mixture is incubated at ambient temperature for 2 hours and then heated at 100° C. for 5 minutes. The enzyme is filtered off through a cotton filter. The filtrate is acidified by addition of hydrochloric acid until a pH of approximately 2 is reached and is stirred at room temperature for 20 minutes. The solution is then neutralized by addition of a saturated sodium hydrogencarbonate solution and is then lyophilized. The mixture is purified on an HPLC column (NH2 column; eluent: $CH_3CN$ 55 $H_2O$ 45). Two fractions are recovered: F1 and F2. The fraction F1 is dissolved in water (10 ml) and acid resin (Dowex 50 W×8) is added. The mixture is stirred at ambient temperature for 8 hours and is then filtered. The aqueous phase is washed with ethyl acetate (3×) and combined with the fraction F2. Lyophilization makes it possible to obtain the expected compound (51 mg, 66%).

High resolution M.S. (ES+): $C_{42}H_{72}O_{35}NaS$ $[M+Na]^+$: Calc.: m/z=1191.3473. Found: m/z=1191.3473. $^{13}C$ NMR (100 MHz, $D_2O$): 100–99.65 ($C1^{II}$, $C1^{III}$, $C1^{IV}$, $C1^{VI}$, $C1^{VII}$); 96.21 ($C1^{1\beta}$); 92.27 ($C1^{I\alpha}$); 85.69 ($C^{V\alpha,\beta}$); 80.44, 77.72, 77.53, 77.40, 77.19, 77.04, 76.59, 74.99, 74.41, 74.26, 73.67, 73.40, 73.24, 73.08, 72.12, 71.89, 71.74, 71.58, 71.26, 71.17, 70.47, 69.68 ($C2^I$, $C3^I$, $C4^I$, $C5^I$, $C2^{II}$, $C3^{II}$, $C4^{II}$, $C5^{II}$, $C2^{III}$, $C3^{III}$, $C4^{III}$, $C5^{III}$, $C2^{IV}$, $C3^{IV}$, $C4^{IV}$, $C5^{IV}$, $C2^V$, $C3^V$, $C4^V$, $C_5^V$, $C_2^{VI}$, $C_3^{VI}$, $C_4^{VI}$, $C5^{VI}$, $C2^{VII}$, $C3^{VII}$, $C4^{VII}$, $C5^{VII}$); 61.42–61 ($C6^I$, $C6^{III}$, $C6^{IV}$, $C6^V$, $C6^{VI}$, $C6^{VII}$); 31.05 ($C6^{II}$).

EXAMPLE 10 a) Methyl(2,3,4,6-tetra-O-acetyl-α-D-glucopyranosyl)-(1→4)-(2,3,6-tri-O-acetyl-α-D-glucopyranosyl)-(1→4)-(2,3-di-O-acetyl-6-bromo-6-deoxy-α-D-glucopyranosyl)-(1→4)-(2,3,6-tri-O-acetyl-α-D-glucopyranosyl)-(1→4)-2,3,6-tri-O-acetyl-α-D-glucopyranoside

A10

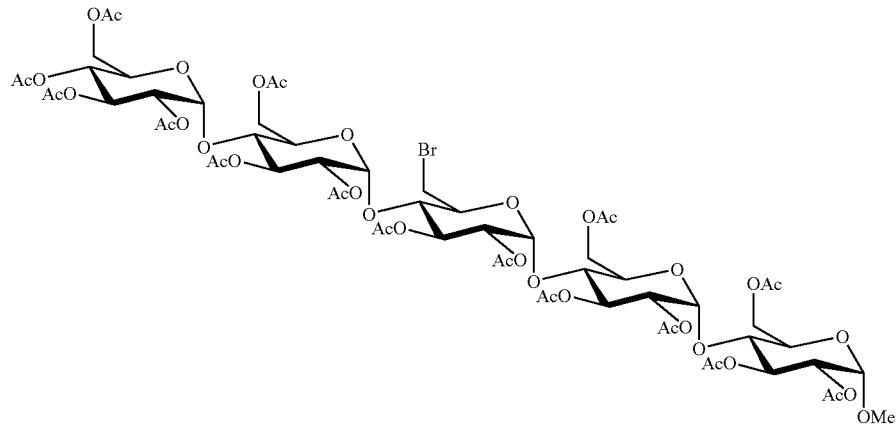

The compound D4 prepared in example 4d) (100 mg, 0.20 mmol) and methyl α-D-glucopyranoside (43.5 mg, 1.1 eq) are dissolved in a phosphate buffer solution (3.7 ml, 0.1M, pH=7.0). cGTase (130 µl) is added. The reaction mixture is incubated at 40° C. for 15 hours and then heated at 100° C. for 5 minutes. The enzyme is filtered off through a cotton filter. The filtrate is acidified by addition of hydrochloric acid until a pH of approximately 2 is reached and is stirred at room temperature for 20 minutes. The solution is then neutralized by addition of ammonia, and the fluoride E1 prepared in example 1e) (112 mg, 1.3 eq), in solution in the buffer (1 ml), and cGTase (129 µl) are added. The mixture is incubated at ambient temperature for 2 hours and is then heated at 100° C. for 5 minutes. The enzyme is filtered off through a cotton filter. The filtrate is acidified by addition of hydrochloric acid until a pH of approximately 2 is reached and is stirred for 20 minutes. The solution is then neutralized by addition of ammonia. The lyophilisate is dissolved in anhydrous pyridine (20 ml), and acetic anhydride (10 ml) and DMAP (<1 mg) are added. The reaction mixture is stirred at 70° C. for 12 hours and then the excess anhydride is neutralized by addition of methanol (10 ml) at 0° C. The reaction mixture is concentrated on a rotary evaporator, the residue is taken up in $CH_2Cl_2$ and the solution is washed with water and then with a saturated $NaHCO_3$ solution. The aqueous phases are extracted with $CH_2Cl_2$ (3 times). The organic phases are combined, dried over $Na_2SO_4$ and evaporated. Purification by fast chromatography ($Et_2O$ and then $Et_2O$ 10 acetone 1) makes it possible to obtain the compound A10 (161 mg, 52%).

$[\alpha]_D$: +105° (c=0.25, chloroform) High resolution M.S. (ES+): $C_{61}H_{83}BrO_{40}Na$ [M+Na]$^+$ Calc.: m/z=1557.3542. Found: m/z=1557.3542. $^1$H NMR (400 MHz, CDCl$_3$):

EXAMPLE 11 a) Preparation of 2,3,6-tri-O-acetyl-α-D-galactopyranosyl-(1→4)-1,2,3,6-tetra-β-D-glucopyranose

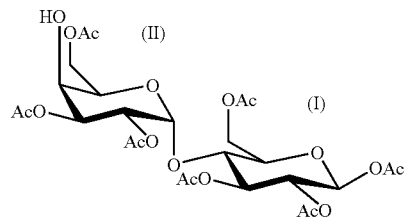

A11

The compound B1 prepared in example 1b) (202 g, 0.32 mmol) is dissolved in anhydrous dichloromethane (8.6 ml), and pyridine (860 µl) is added. The reaction is cooled to 0° C. and triflic anhydride (143 µl) is added. The reaction mixture is stirred for 30 minutes and washed under cold conditions with: water, a saturated sodium hydrogencarbonate solution and an acidic potassium hydrogensulfate solution. The organic phase is dried over anhydrous sodium sulfate and evaporated to dryness. The residue is taken up in distilled dimethylformamide (12 ml) and tetrabutyl-ammonium nitrite is added (922 mg). The reaction mixture is stirred at ambient temperature for 12 hours, diluted with ethyl acetate and then washed successively with a saturated sodium chloride solution and with water. The organic phase is dried over anhydrous sodium sulfate and evaporated to dryness. The expected compound is purified by fast chromatography (1. EtOAc 1 PE 1; 2. EtOAc 1.5 PE 1) (192 mg, 95%).

$[\alpha]D$: 73.3° (c=1, chloroform) High resolution M.S. (ES+): $C_{26}H_{36}O_{18}Na$ [M+Na]$^+$Calc.: m/z=659.1799. Found: m/z=659.1813. High resolution M.S. (ES+):

|  | Chemical shifts | | | | | | | Coupling constants | | | | | | |
|---|---|---|---|---|---|---|---|---|---|---|---|---|---|---|
| A10 | H1 | H2 | H3 | H4 | H5 | H6a | H6b | J12 | J23 | J34 | J45 | J5a | Jab | J5b |
| Unit I | 4.82 | 4.75 | 5.51 | 3.95a | 3.97a | 4.45 | 4.30 | 3.6 | 10.1 | 9.0 | 7.0 | 3.3 | 12.3 | 2.8 |
| Unit II* | 5.29 | 4.70 | 5.39 | 3.89 | 4.00 | 4.49 | 4.25 | 4.1 | 10.3 | 9.2 | 9.4 | 3.3 | 12.6 | 4.0 |
| Unit III | 5.30 | 4.72 | 5.40 | 3.96a | 3.98a | 3.74a | 3.70a | 4.2 | 10.3 | 8.6 | 7.5 | 2.1 | 11.5 | <1 |
| Unit IV* | 5.33 | 4.73 | 5.35 | 3.97 | 3.90 | 4.22 | 4.01 | 4.2 | 10.3 | 8.7 | 9.6 | 3.8 | 12.4 | 3.1 |
| Unit V | 5.40 | 4.84 | 5.36 | 5.05 | 3.90 | 4.56 | 4.23 | 4.0 | 10.6 | 9.5 | 10.3 | 2.7 | 12.3 | 3.5 | aDegenerate protons;
*Uncertainty between the two sugar units

OCH$_3$: 3.41 COCH$_3$: 2.17, 2.16, 2.14, 2.07, 2.07, 2.04, 2.02, 2.01, 2.00, 1.98, 1.97, 1.96 $^{13}$C NMR (100 MHz, CDCl$_3$): 170.45–169.56 (COCH$_3$); 96.58, 95.87, 95.65, 95.53 (C1$^I$, C1$^{II}$, C1$^{III}$, C1$^{IV}$, C$_1^V$); 74.18, 76.79, 73.67, 72.64, 72.34, 71.73, 71.26, 70.36, 69.97, 69.40, 69.11, 68.94, 68.77, 68.45, 67.98, 67.54 (C2$^I$, C3$^I$, C4$^I$, C5$^I$, C2$^{II}$, C3$^{II}$, C4$^{II}$, C5$^{II}$, C2$^{III}$, C3$^{III}$, C4$^{III}$, C5$^{III}$, C2$^{IV}$, C3$^{IV}$, C4$^{IV}$, C5$^{IV}$, C2$^V$, C3$^V$, C4$^V$, C$_5^V$); 63.00, 62.71, 62.56, 61.36 (C6$^I$, C6$^{II}$, C6$^{IV}$, C6$^V$); 55.53 (OCH$_3$); 33.45 (C6$^{III}$); 20.83–20.51 (COCH$_3$).

$C_{26}H_{36}O_{18}K$ [M+K]$^+$ Calc.: m/z=675.1539. Found: m/z=675.1542. $^1$H NMR (300 MHz, CDCl$_3$, 303° K): 5.70 (H1$^I$; d; J$_{1,2}$=8.2 Hz); 5.38 (H1$^{II}$; d; J$_{1,2}$=3.6 Hz); 5.38 (H1$^{II}$; J$_{1,2}$=3.7 Hz); 5.24 (H3$^I$; dd≈t; J$_{2,3}$≈J$_{3,4}$9.3 Hz); 5.18 (H3$^{II}$; H2$^I$; dq); 4.94 (H2$^I$; dd≈t; J$_{2,3}$≈9.3 Hz); 4.45 (H6a$^I$; dd; J$_{5,6a}$=2.4 Hz; J$_{6a,6b}$=12.2 Hz); 4.31 (H6a$^{II}$; dd; J$_{5,6a}$=6.76 Hz; J$_{6a,6b}$=11.3 Hz); 4.15 (H6b$^I$; dd; J$_{5,6b}$=5.11 Hz); 4.11 (H6b$^{II}$, dd, J$_{5,6b}$=3.66 Hz); 4.07 (H4$^{II}$; m); 3.99 (H4$^I$; dd; H$_{4,5}$=8.59 Hz); 3.96 (H5$^{II}$; m); 3.78 (H5$^I$; m); 2.08, 2.07, 2.06, 2.02, 1.98, 1.97 (CH$_3$CO; s; Intg=21 H). $^{13}$C NMR (75 MHz, CDCl$_3$, 303° K):$^{128}$ 170.84, 170.69, 170.39, 170.03, 169.78, 169.54, 168.75 (COCH$_3$); 96.26 (C1$^{II}$); 91.26 (C1$^I$);

75.26, 73.25, 72.20, 70.97, 69.13, 68.64, 67.34, 67.17 (C2$^I$, C3$^I$, C4$^I$, C5$^I$, C2$^{II}$, C3$^{II}$, C4$^{II}$) C5$^{II}$); 62.71, 62.69 (C6$^I$, C6$^{II}$); 20.75, 20.71, 20.65, 20.61, 20.44 (COCH$_3$)

b) Preparation of 4-azido-4-deoxy-2,3,6-tri-O-acetyl-α-D-glucopyranosyl-(1→4)-1,2,3,6-tetra-O-acetyl-β-D-glucopyranose

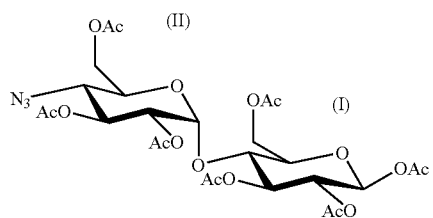

B11

The compound A11 prepared in example 11a) (110 mg, 0.17 mmol) is dissolved in anhydrous dichloromethane (4 ml), and pyridine (400 µl) is added. The reaction mixture is cooled to −15° C. and triflic anhydride (70 µl) is added. The reaction mixture is stirred at −15° C. for 30 minutes and then at ambient temperature for 2 hours. The mixture is then washed under cold conditions with: water, a saturated sodium hydrogen-carbonate solution and an acidic potassium hydrogen-sulfate solution. The organic phase is dried over anhydrous sodium sulfate and evaporated to dryness. The residue is taken up in distilled dimethylformamide (0.9 ml) and sodium azide (64 mg) is added. The reaction mixture is stirred at ambient temperature for 12 hours and is then diluted with ethyl acetate, washed with water, dried over anhydrous sodium sulfate and evaporated. The expected compound is purified by fast chromatography (EtOAc/PE: 4/1) (102 mg, 91%).

$[\alpha]_D$: +181° (c=1, chloroform) High resolution M.S. (ES+): C$_{26}$H$_{35}$N$_3$O$_{17}$Na [M+Na]$^+$ Calc.: m/z=684.1864. Found: m/z=684.1863. High resolution M.S. (ES+): C$_{26}$H$_{35}$N$_3$O$_{17}$K [M+K]$^+$ Calc.: m/z=700.1604. Found: m/z=700.1591. $^1$H NMR (300 MHz, CDCl$_3$, 303° K): 5.70 (H1$^I$; d; J$_{1,2}$=7.8 Hz); 5.32 (H3$^{II}$; dd≈t; J$_{3,4}$=9.7 Hz); 5.31 (H1$^{II}$; d); 5.25 (H3$^I$; dd≈t; J$_{2,3}$=8.2 Hz); 4.93 (H2$^I$; dd≈t; J$_{2,3}$=9.5 Hz); 4.77 (H2$^{II}$; dd; J$_{1,2}$=3.8 Hz; J$_{2,3}$=10.4 Hz); 4.40 (H6a*; dd; J$_{5,6a}$=3 Hz; J$_{6a,6b}$=12.2 Hz); 4.30 (H6a*; dd; J$_{5,6a}$=2.1 Hz; J$_{6a,6b}$=12.2 Hz); 4.19 (H6b*; dd; J$_{5,6b}$=3.66 Hz); 4.15 (H6b*; dd; J$_{5,6b}$=4.38 Hz); 3.95 (H4$^I$; dd; J$_{4,5}$=10.1 Hz); 3.79 (H5$^I$; m); 3.70 (H5$^{II}$; m); 3.56 (H4$^{II}$; dd≈t; J$_{4,5}$=10.4 Hz); 2.08, 2.07, 2.06, 2.02, 1.98, 1.97 (CH$_3$CO; s; intg=18 H). $^{13}$C NMR (75 MHz, CDCl$_3$, 303° K): 170.67, 170.32, 169.91, 169.56, 169.41, 168.70 (COCH$_3$); 95.97 (C1$^{II}$); 91.26 (C1$^I$); 75.16, 73.05, 72.71, 70.92, 70.16, 69.94, 68.98 (C2$^I$, C3$^I$, C4$^I$, C5$^I$, C2$^{II}$, C3$^{II}$, C5$^{II}$); 62.46, 62.32 (C6$^I$, C6$^{II}$); 60.04 (C4$^{II}$); 20.73, 20.58, 20.48 (COCH$_3$).

*: uncertainty between the unit I and II.

c) Preparation of 4-azido-4-deoxy-2,3,6-tri-O-acetyl-α-D-glucopyranosly-(1→4)-2,3,6-tri-O-α-D-glucopyranosyl fluoride

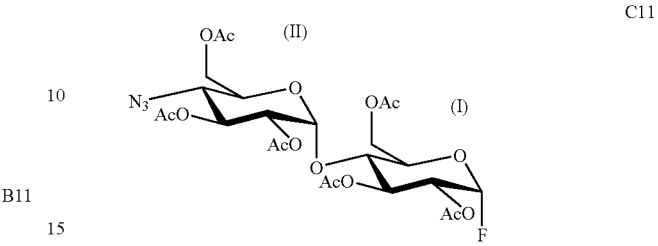

C11

The reaction is carried out at 0° C. in a plastic container.

The compound B11 prepared in example 11b) (100 mg, 0.15 mmol) is dissolved in a solution of hydrogen fluoride in pyridine (7/3, v/v, 3 ml). After stirring for half an hour, the reaction mixture is diluted with dichloromethane and then poured onto an ice-cold 3M ammonia solution.

After separation by settling, the organic phase is washed twice with an ice-cold saturated sodium hydrogencarbonate solution. The organic phase is subsequently dried over anhydrous sodium sulfate and then evaporated using a rotary evaporator.

Fast chromatography (EtOAc/PE: 1/1) using a silica gel neutralized beforehand with triethylamine makes it possible to obtain the expected fluoride (71 mg, 75%).

$[\alpha]_D$: +112° (c=0.3, chloroform) High resolution M.S. (ES+): C$_{24}$H$_{32}$FN$_3$O$_{15}$Na [M+Na]$^+$ Calc.: m/z=644.1715. Found: m/z=644.1720. High resolution M.S. (ES+): C$_{24}$H$_{32}$FN$_3$O$_{15}$K [M+K]$^+$ Calc.: m/z=660.1455. Found: m/z=660.1470. $^1$H NMR (300 MHz, CDCl$_3$, 303° K): 5.61 (H1$^I$; dd; J$_{1,2}$=2.7 Hz; J$_{1,F}$=53.2 Hz); 5.50 (H3$^I$; dd; J$_{2,3}$=10.1 Hz; J$_{3,4}$=9.0 Hz); 5.35 (H1$^{II}$; d); 5.33 (H3$^{II}$; dd≈t; J$_{3,4}$=9.9 Hz); 4.80 (H2$^I$; ddd; J$_{2,F}$=26.7 Hz); 4.78 (H2$^{II}$; dd; J$_{1,2}$=4.0 Hz; J$_{2,3}$=10.4 Hz); 4.40 (H6a$^{II}$; dd; J$_{5,6a}$=2.2 Hz; J$_{6a,6b}$=12.4 Hz); 4.31 (H6a$^{II}$; dd; J$_{5,6a}$=2.2 Hz; J$_{6a,6b}$=12.4 Hz); 4.21 (H6b$^{II}$; J$_{5,6b}$=3.5 Hz); 4.16 (H6b$^I$; J$_{5,6b}$=3.8 Hz); 4.13 (H5$^I$; m); 3.95 (H4$^I$; dd≈t; J$_{4,5}$=9.7 Hz); 3.70 (H5$^{II}$; m); 3.58 (H4$^{II}$; dd≈t; J$_{4,5}$=10.4 Hz); 2.12, 2.10, 2.07, 2.04, 1.99 (CH$_3$CO; s; intg=18 H). $^{13}$C NMR (75 MHz, CDCl$_3$, 303° K): 170.23, 170.03, 169.59, 169.42 (COCH$_3$); 103.56 (C1$^I$; d; J$_{C,F}$=229.3 Hz); 95.89 (C1$^{II}$); 71.88, 71.71, 70.70, 70.38, 70.28, 70.23, 70.16, 69.89, 69.01 (C2$^I$, C3$^I$, C4$^I$, C5$^I$, C2$^{II}$, C3$^{II}$, C5$^{II}$); 62.22, 61.98 (C6$^I$, C6$^{II}$); 60. 0 (C4$^{II}$); 20.80, 20.70, 20.53, 20.43 (COCH$_3$).

d) Preparation of 4-azido-4-deoxy-α-D-glucopyranosyl-(1→4)-α-D-glucopyranosyl fluoride

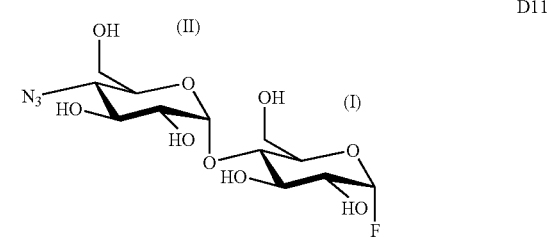

D11

The compound C11 prepared in the preceding stage (34 mg, 51.5 μmol) is dissolved in methanol (10 ml). A solution of sodium methoxide in methanol (1M, 100 μl) is added. After stirring at ambient temperature for 4 hours, the reaction mixture is cooled to 0° C. and then neutralized with Amberlite IRN 120H+ resin. After filtration, the compound is concentrated and the residue is taken up in water and lyophilized (19 mg, 100%). This compound is used without additional purification.

$[\alpha]_D$: 154° (c=0.87, water) High resolution M.S. (ES+): $C_{12}H_{20}FN_3O_9Na$ [M+Na]+ Calc.: m/z=392.1081. Found: m/z=392.1081. $^1$H NMR (400 MHz, $D_2O$):

| C11 | Chemical shifts | | | | | | | Coupling constants | | | | | | | | |
|---|---|---|---|---|---|---|---|---|---|---|---|---|---|---|---|---|
| | H1 | H2 | H3 | H4 | H5 | H6a | H6b | J12 | J23 | J34 | J45 | J5a | Jab | J5b | J1F | J2F |
| Unit I | 5.54 | 3.50 | 3.85 | 3.61 | 3.79 | 3.71 | 3.64 | 2.8 | 9.9 | 9.4 | 9.9 | 2.1 | 12.6 | 4.2 | 53.3 | 26.5 |
| Unit II | 5.30 | 3.50 | 3.68 | 3.30 | 3.54 | 3.59 | 3.55 | 3.9 | 9.9 | 10.2 | 10.1 | 2.8 | 12.6 | 3.9 | | |

$^{13}$C NMR (100 MHz, $CDCl_3$): 107.46 ($C1^I$; d; $J_{C,F}$=229.4 Hz); 100.14 ($C1^{II}$); 76.02, 73.19, 72.94, 72.30, 71.97, 71.55, 71.33, 71.09 ($C2^I$, $C3^I$, $C4^I$, $C5^I$, $C2^{II}$, $C3^{II}$, $C5^{II}$); 61.90, 60.97 ($C6^I$, $C6^{II}$); 60.34 ($C4^{II}$).

EXAMPLE 12 a) Preparation of (2,3,6-tri-O-acetyl-4-azido-4-deoxy-α-D-glucopyranosyl)-(1→4)-(2,3,6-tri-O-acetyl-α-D-glucopyranosyl)-(1→4)-(di-O-acetyl-6-bromo-6-deoxy-α-D-glucopyranosyl)-(1→4)-1,2,3,6-tetra-O-acetyl-D-glucopyranose

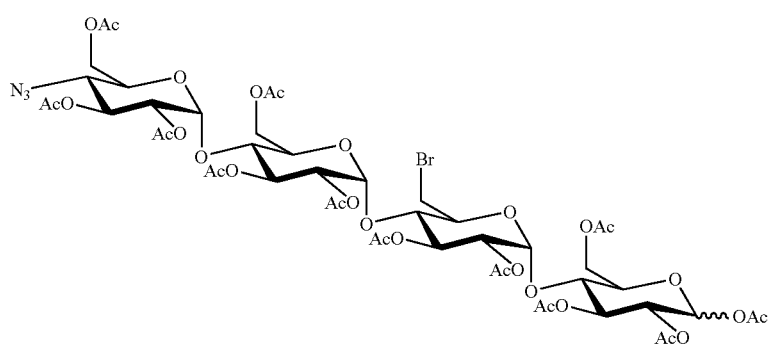

A12

The fluoride D11 prepared in example 11d) (90.9 mg, 0.25 mmol) and 6-bromo-6-deoxy-α-D-glucopyranosyl-(1→4)-D-glucopyranose (90.9 mg, 0.22 mmol) are dissolved in a phosphate buffer solution (0.1M, pH=7, 9 ml) and cGTase (270 μl) is added. The reaction mixture is incubated at ambient temperature for 3 hours and is then lyophilized. The solid is taken up in distilled pyridine (10 ml) and acetic anhydride is added (10 ml), along with a catalytic amount of 4,4-dimethylaminopyridine (DMAP, ≈1 mg). The reaction is stirred at 70° C. for 12 hours and then the reaction medium is cooled and the excess anhydride is destroyed by slow addition of methanol at 0° C. (5 ml). The mixture Calc.: m/z=1089.3234. Found: m/z=1089.3233. $^1$H NMR (400 MHz, $CDCl_3$):

|  | Chemical shifts | | | | | | | Coupling constants | | | | | | |
| --- | --- | --- | --- | --- | --- | --- | --- | --- | --- | --- | --- | --- | --- | --- |
| A12 | H1 | H2 | H3 | H4 | H5 | H6a | H6b | J12 | J23 | J34 | J45 | J5a | Jab | J5b |
| Unit Iα | 6.22 | 4.93 | 5.48 | 4.00 | 4.11 | 4.48 | 4.26 | 3.7 | 10.0 | 8.9 | 9.8 | 2.7 | 12.4 | 3.9 |
| Unit Iβ | 5.74 | 4.94 | 5.26 | 3.99 | 3.85 | 4.45 | 4.28 | 8.0 | 9.2 | 8.4 | 9.9 | 3.2 | 12.4 | 4.5 |
| Unit IIα, β | 5.31 | 4.74 | 5.42 | 3.99 | 3.98 | 3.76 | 3.68 | 3.8 | 10.1 | 9.2 | — | 5.0 | 11.5 | — |
| Unit IIα, β | 5.33 | 4.72 | 5.39 | 3.97 | 3.98 | 3.76 | 3.68 | 4.1 | 10.1 | 8.9 | — | 5.0 | 11.5 | — |
| Unit III | 5.30 | 4.72 | 5.33 | 3.91 | 3.90 | 4.53 | 4.15 | 4.2 | 10.0 | 9.2 | — | — | 12.5 | 3.4 |
| Unit IV | 5.35 | 4.78 | 5.35 | 3.59 | 3.68 | 4.30 | 4.20 | 4.1 | 10.2 | 10.0 | 10.4 | 3.2 | 12.4 | 4.0 |

$CH_3CO$: 2.20, 2.14, 2.13, 2.11, 2.08, 2.04, 2.01, 2.00, 1.99, 1.98, 1.96. $^{13}C$ NMR (100 MHz, $CDCl_3$): 170.82, 170.56, 170.36, 169.99, 169.53 ($\underline{C}OCH_3$); 96.01, 95.84, 95.56 ($C1^{II}$, $C1^{III}$, $C1^{IV}$); 91.21 ($C1^{Iβ}$); 88.82 ($C1^{Iα}$); 75.17, 74.42, 73.54, 73.34, 72.93, 72.40, 72.17, 71.69, 71.10, 70.97, 70.33, 70.14, 70.00, 69.73, 69.17, 68.87 ($C2^I$, $C3^I$, $C4^I$, $C5^I$, $C2^{II}$, $C3^{II}$, $C4^{II}$, $C5^{II}$, $C2^{III}$, $C3^{III}$, $C4^{III}$, $C5^{III}$, $C2^{IV}$, $C3^{IV}$, $C5^{IV}$); 6 2.57–62.21 ($C6^I$, $C6^{III}$, $C6^{IV}$); 59.99 ($C4^{IV}$); 33.44 ($C6^{II}$); 20.84–20.53 ($CO\underline{C}H_3$).

A13

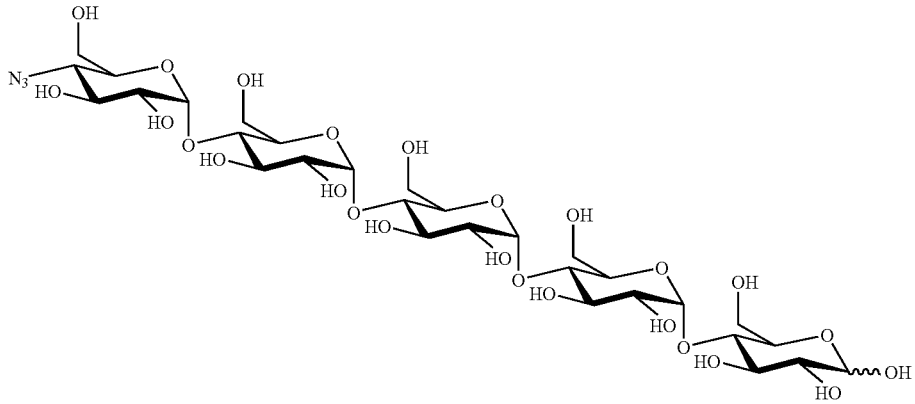

The fluoride D11 prepared in example 11d) (10 mg, 27.1 μmol) is dissolved in phosphate buffer (50 mM, pH =7, 95 μl), and methanol (156 μl) and *Aspergillus oryzae* α-amylase, in solution in the buffer (54 U, 51 μl), are added. The mixture is incubated at room temperature for 2 hours and is then heated at 100° C. for 5 minutes and filtered. The mixture is concentrated and co-evaporated with water. The expected compound is purified on Sep-pack C18® (15 mg, 65%).

High resolution M.S. (ES+): $C_{30}H_{51}N_3O_{25}Na$ [M+Na]$^+$ Calc.: m/z=876.2709. Found: m/z=876.2713. $^1H$ NMR (300 MHz, $D_2O$, 303° K): 5.30–5.25 ($H1^{II}$, $H1^{III}$, $H1^{IV}$, $H1^V$; m); 5.10 ($H1^{Iα}$; d; 3.7 Hz); 4.35 ($H1^{Iβ}$; d; 8.0 Hz); 3.87–3.42 ($H2^{Iα}$, $H2^{II}$, $H2^{III}$, $H2^{IV}$, $H2^V$, $H3^I$, $H3^{II}$, $H3^{III}$, $H3^{IV}$, $H3^V$, $H4^I$, $H4^{II}$, $H4^{III}$, $H4^{IV}$, $H5^I$, $H5^{II}$, $H5^{III}$, $H5^{IV}$, $H5^V$, $H6a^I$, $H6a^{II}$, $H6a^{III}$, $H6a^{IV}$, $H6a^V$, $H6b^I$, $H6b^{II}$, $H6b^{III}$, $H6b^{IV}$, $H6b^V$; m); 3.15 ($H2^{Iβ}$; dd; $J_{2,3}$=9.1 Hz); 3.32 ($H4^V$; dd≈

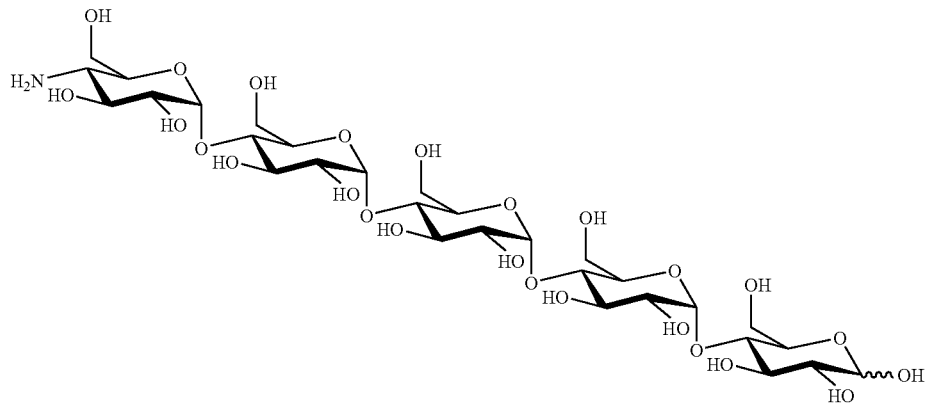

B13

Hydrogen sulfide is bubbled for 30 minutes into a pyridine/water mixture (1/1, 3 ml) comprising the compound A13 (15 mg, 17.6 μmol). The round-bottomed flask is subsequently hermetically sealed and the reaction medium is stirred at ambient temperature for 12 hours and then filtered, concentrated and co-evaporated evaporated with water. The expected compound is purified on Sep-pak C18® and lyophilized (14 mg, 96%).

High resolution M.S. (ES+): $C_{30}H_{54}NO_{25}$ $[M+H]^+$ Calc.: m/z=828.2983. Found: m/z=828.2985. $^1$H NMR (300 MHz, $D_2O$, 303° K): 5.32–5.26 (H1$^{II}$, H1$^{III}$, H1$^{IV}$, H1$^{V}$; m); 5.10 (H1$^{I\alpha}$; d; 3.56 Hz); 4.52 (H1$^{I\beta}$; d; 8.0 Hz); 3.86–3.41 (H2$^{I\beta}$, H2$^{II}$, H2$^{III}$, H2$^{IV}$, H2$^{V}$, H3$^{I}$, H3$^{II}$, H3$^{III}$, H3$^{IV}$, H3$^{V}$, H4$^{I}$, H4$^{II}$, H4$^{III}$, H4$^{IV}$, H5$^{I}$, H5$^{II}$, H5$^{III}$, H5$^{IV}$, H5$^{V}$, H6a$^{I}$, H6a$^{II}$, H6a$^{III}$, H6a$^{IV}$, H6a$^{V}$, H6b$^{I}$, H6b$^{II}$, H6b$^{III}$, H6b$^{IV}$, H6b$^{V}$; m); 3.14 (H2$^{I\beta}$; dd; $J_{2,3}$=9.4 Hz); 2.89 (H4$^{V}$; dd≈ c) Preparation of 4-deoxy-4-(6-nitroveratryloxycarbonylamino)-α-D-glucopyranosyl-(1→4w)-α-D-glucopyranosyl-(1→4)-α-D-glucopyranosyl-(1→4)-α-D-glucopyranosyl-(1→4)-D-glucopyranose

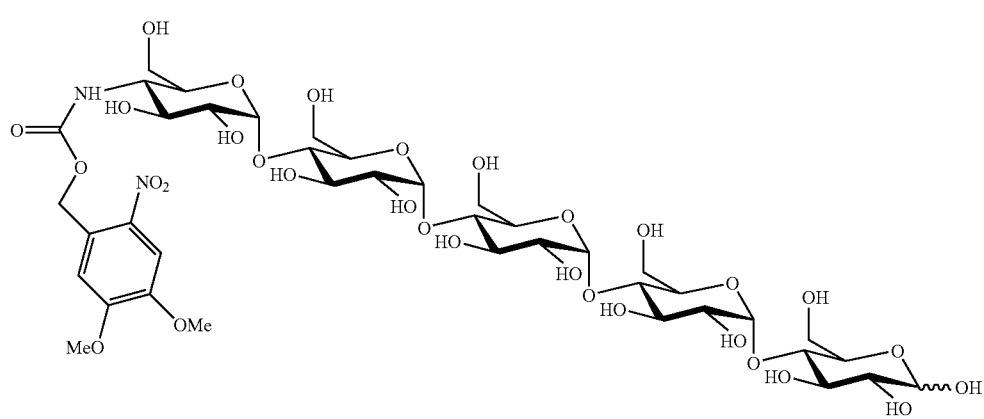

C13

Pyridine (5 μl) is added to the compound B13 prepared in example 13b) (10 mg, 12.1 μmol) dissolved in anhydrous DMF (300 μl). The mixture is cooled to 0° C. and 6-nitroveratryl chloroformate (3.2 mg, 1 eq) and a catalytic amount of DMAP are added. The mixture is stirred at ambient temperature for 4 hours and chloroformate (3.2 mg) is added. The reaction mixture is heated at 70° C. for 12 hours and chloroformate (3.2 mg) is added. The mixture is then heated at 100° C. for 4 hours and is cooled to 0° C. Acetone (3 ml) is added and the precipitate formed is filtered off, dissolved in water, purified on Sep-pack C18® and lyophilized (9 mg, 70%).

What is claimed is:

1. A disaccharide of formula I:

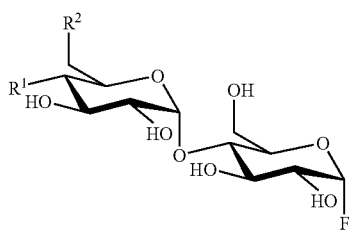

derived from α-maltosyl fluoride, wherein:
$R^1$ and $R^2$, identical or different, each represents a functional organic group, non protected or protected, attached to the glycoside unit via an atom selected from the group consisting of a nitrogen atom, an oxygen atom, a sulfur atom and a halogen atom; or else
$R^1$ and $R^2$ together form a functional organic group, non protected or protected, attached to the glycoside unit via two atoms selected from the group consisting of oxygen, sulfur and nitrogen atoms,
it being understood that $R^1$ does not represent a hydroxyl group.

2. The disaccharide of claim 1, wherein $R^2$ represents hydroxyl.

3. The disaccharide of claim 1, wherein $R^1$ is selected from the group consisting of a chlorine atom, a bromine atom, an iodine atom, an acetal group, a hemiacetal group, an ester group, an ether group, a sulfonate group, a carbamate group, a carbonate group, an amine group, an amide group, an azide group, a urea group, a thioacetate group, a disulfide group, a thiourea group and one of these groups in a protected form.

4. The disaccharide of claim 1, wherein $R^2$ is selected from the group consisting of a fluorine atom, a chlorine atom, a bromine atom, an iodine atom, an acetal group, a hemiacetal group, an ester group, an ether group, a sulfonate group, a carbamate group, a carbonate group, an amine group, an amide group, an azide group, a urea group, a thioacetate group, a disulfide group, a thiourea group and one of these groups in a protected form.

5. The disaccharide of claim 1, wherein $R^1$ and $R^2$ together form a protective group for a diol functional group.

6. The disaccharide of claim 1, wherein $R^1$ and $R^2$ together form an alkylidenedioxy group, or an alkylidenedioxy group substituted by aryl.

7. The disaccharide of claim 1, wherein $R^1$ and $R^2$ together form an O-isopropylidene or O-benzylidene group.

8. The disaccharide of claim 2, wherein $R^1$ represents 2-tetrahydropyranyl.

9. The disaccharide of claim 1, wherein $R^1$ represents 2-tetrahydropyranyl and $R^2$ represents bromo or another halogen.

10. The disaccharide of claim 1, wherein $R^1$ and $R^2$ independently represent non substituted or substituted amino or $-N_3$.

11. The disaccharide of claim 1, wherein $R^1$ represents non substituted or substituted azido or amino, and $R^2$ represents OH.

12. A method for implementing a transglycosylation reaction catalyzed by a glycoside hydrolase, or a transfer reaction catalyzed by a transglycosylase, said method making use of the disaccharide of claim 1, as a glycosyl donor.

13. The method of claim 12, wherein the glycoside hydrolase belongs to family 13 of the glycoside hydrolases.

14. The method of claim 12, wherein the glycoside hydrolase is a cyclodextrin glycosyltransferase.

15. The method of claim 12, for the preparation of oligosaccharides or polysaccharides, involving at least one condensation reaction between disaccharide and the pyranosyl unit of a glycosyl acceptor.

16. The method of claim 15, wherein the glycosyl acceptor is pullulan.

17. The method of claim 15, wherein each condensation reaction results from the reaction of a hydroxyl of a nonreducing pyranosyl unit of the glycosyl acceptor with the unit of maltosyl type.

18. The method of claim 17, wherein each condensation reaction results from the reaction of a hydroxyl of a non reducing pyranosyl unit of the glycosyl acceptor with the anomeric carbon of the maltosyl unit carrying the fluorine atom.

19. A process for the preparation of oligosaccharides or polysaccharides comprising the reaction of at least one disaccharide of formula I of claim 1 with a glycosyl acceptor, in the presence of an enzyme selected from enzyme of glycoside hydrolase type and of transglycosylase type.

20. The process of claim 19, wherein the glycoside hydrolase belongs to family 13 of the glycoside hydrolases.

21. The process of claim 20, wherein the glycoside hydrolase is a cyclodextrin glycosyltransferase.

22. The process as claimed in claim 16, characterized in that the glycosyl acceptor exhibits, at the nonreducing end, a pyranosyl unit exhibiting at least one functional group capable of reacting with the disaccharide of formula I.

23. The process of claim 22, wherein the glycosyl acceptor is pullulan.

24. The process of claim 22, wherein the reacting functional group of the pyranosyl unit is a hydroxyl functional group in the 2, 3, 4 or 6 position.

25. The process of claim 22, wherein the reacting functional group of the pyranosyl unit is a hydroxyl functional group in the 4 position.

* * * * *